(12) United States Patent
Blackburn et al.

(10) Patent No.: US 7,109,326 B2
(45) Date of Patent: Sep. 19, 2006

(54) HALO-ALKOXYCARBONYL PRODRUGS

(75) Inventors: Brent Blackburn, San Francisco, CA (US); Alan G. Olivero, Half Moon Bay, CA (US); Kirk Robarge, San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 10/854,388

(22) Filed: May 25, 2004

(65) Prior Publication Data

US 2004/0220401 A1 Nov. 4, 2004

Related U.S. Application Data

(63) Continuation of application No. 10/290,793, filed on Nov. 8, 2002, now abandoned, and a continuation of application No. 09/059,808, filed on Apr. 14, 1998, now abandoned.

(60) Provisional application No. 60/042,228, filed on Apr. 15, 1997.

(51) Int. Cl.
C07D 243/24 (2006.01)
(52) U.S. Cl. .................................... 540/506
(58) Field of Classification Search ................ 540/506
See application file for complete search history.

(56) References Cited

U.S. PATENT DOCUMENTS

| | | | |
|---|---|---|---|
| 4,046,887 | A | 9/1977 | Paris et al. |
| 4,381,307 | A | 4/1983 | Sloan |
| 4,760,057 | A | 7/1988 | Alexander et al. |
| 4,851,426 | A | 7/1989 | Ladkani et al. |
| 5,001,115 | A | 3/1991 | Sloan |
| 5,446,056 | A | 8/1995 | Wityak et al. |
| 5,466,811 | A | 11/1995 | Alexander |
| 5,478,945 | A | 12/1995 | Sato et al. |
| 5,554,643 | A | 9/1996 | Horwell et al. |
| 5,576,444 | A | 11/1996 | Himmelsbach et al. |
| 5,589,588 | A | 12/1996 | Toce |
| 5,599,793 | A | 2/1997 | Chirgadze et al. |

FOREIGN PATENT DOCUMENTS

| | | |
|---|---|---|
| EP | 529858 | 3/1993 |
| EP | 540051 | 5/1993 |
| EP | 540574 | 5/1993 |
| EP | 743320 | 11/1996 |
| WO | WO 93/08174 | 4/1993 |
| WO | WO 94/17817 | 8/1994 |
| WO | WO 95/04057 | 2/1995 |
| WO | WO 95/13274 | 5/1995 |
| WO | WO 95/14682 | 6/1995 |
| WO | WO 95/29189 | 11/1995 |
| WO | WO 95/35312 | 12/1995 |
| WO | WO 95/35313 | 12/1995 |
| WO | WO 96/11697 | 4/1996 |
| WO | WO 96/24609 | 8/1996 |
| WO | WO 96/32110 | 10/1996 |

OTHER PUBLICATIONS

Alexander, J. et al., "(Acyloxy)alkyl Carbamates as Novel Bioreversible Prodrugs for Amines: Increased Permeation through Biological Membranes" *Journal of Medicinal Chemistry* 31:318-322 (1988).

Aoki, T. et. al., "The Anti-Platelet and Anti-Thrombotic Effects of FK633, A Peptide-Mimetic GPIIB/IIA Antagonist" *Thrombosis Research* 81(4) :439-450 (1996).

Barker, P. L. et al., "Cyclic RGD Peptide Analogues as Antiplatelet Antithrombotics" *Journal Medicinal Chemistry* 35:2040-2048 (1992).

Bercz, J. P. et al., "Repeated-Dose and Subchronic Toxicity Studies of 2,2,2-Trichloroethanol in Sprague-Dawley Rats" *Journal of the American College of Toxicology* 10(2) :223-232 (1991).

Betrand, J. A. et al., "Inhibition of Trypsin and Thrombin by Amino(4-amidinophenyl)methanephosphonate Diphenyl Ester Derivatives: X-ray Structures and Molecular Models" *Biochemistry* 35:3147-3155 (1996).

Bondinell, W. E. et al., "Design of a Potent and orally Active Nonpeptide Platelet Fibrinogen Receptor (GPIIb/IIIa) Antagonist" *Bioorganic & Medicinal Chemistry* 2(9) :897-908 (1994).

Bovy, P. R. et al., "Design of Orally Active, Non-Peptide Fibrinogen Receptor Antagonists. An Evolutionary Process from the RGD Sequence to Novel Anti-Platelet Aggregation Agents" *Boorganic & Medicinal Chemistry* 2(9) :881-895 (1994).

Carteaux, J-P et al., "RO 44-9883, a New Non-Peptidic GPIIb-GPIIIa Antagonist Prevents Platelets Loss in a Guinea Pig Model of Extracorporeal Circulation" *Thrombosis and Haemostasis* 70(5) :817-821 (1993).

Cook, N.S. et al., "Platelet Aggregation and Fibrinogen Binding in Human, Rhesus Monkey, Guinea-Pig, Hamster and Rat Blood: Activiation by ADP and a Thrombin Receptor Peptide and Inhibition by Glycoprotein IIb/IIIa Antagonists" *Thrombosis and Haemostasis* 70(3) :531-539 (1993).

Cox, D. et al., "Pentamidine Is a Specific, Non-Peptide, GPIIb/IIIa Antagonist" *Thrombosis and Haemostasis* 75(3) :503-9 (1996).

Dickneite, G. et al., "Pharmacological Characterization of a New 4-Amidinophenyl-Alanine Thrombine-Inhibitor (CRC 220)" *Thrombosis Research* 77(4) :357-368 (1995).

Eldred, C. D. et al., "Orally Active Non-Peptide Fibrinogen Receptor (GpIIb/IIIa) Antagonists: Identification of 4- [4- [4-(Aminoimino-methyl)phenyl]-1-piperazinyl]-1-piperidineacetic Acid as a Long-Acting, Broad-Spectrum Antithrombotic Agent" Journal of Medicinal Chemistry 37:3882-3885 (1994).

(Continued)

*Primary Examiner*—Bruck Kifle
(74) *Attorney, Agent, or Firm*—David W Evans

(57) ABSTRACT

Halo-alkoxycarbonyl derivatives are provided as prodrug moieties for pharmaceutical agents containing a basic or polar nitrogen containing functionality. The prodrugs are provided as pharmaceutical compositions as well as in methods of treatment.

5 Claims, 7 Drawing Sheets

OTHER PUBLICATIONS

Frederick, L. G. et al., "The Protective Dose of the Potent GpIIIb/IIIa Antagonist SC-54701A Is Reduced When Used in Combination With Aspirin and Heparin in a Canine Model of Coronary Artery Thrombosis" *Circulation* 93(1) :129-134 (1996).

Greene, T.W. *Protective Groups in Organic Synthesis*, John Wiley & sons pp. 218-224 (1981).

Hara, T. et al., "DX-9065a, a New Synthetic, Potent Anticoagulant and Selective Inhibitor for Factor Xa" *Thrombosis and Haemostasis* 71(3) :314-319 (1994).

Hodohara, K. et al., "Amidinonaphthol derivatives directly inhibit the ligand binding on platelet glycoprotein IIb-IIIa" *Pathophysiology* 2:145-151 (1995).

Mack, H. et al., "Design, Synthesis and Biological Activity of Novel Rigid Amidino-Phenylalanine Derivatives as Inhibitors of Thrombin" *Journal of Enzyme Inhibition* 9:73-86 (1995).

McDowell et al., "From Peptide to Non-Peptide. 1. The Elucidation of a Bioactive Conformation of the Arginine-Glycine-Aspartic Acid Recognition Sequence" *J. Am. Chem. Soc.* 116:5069-5076 (1994).

McDowell et al., "From Peptide to Non-Peptide. 2. The de Novo Design of Potent, Non-Peptidal Inhibitors of Platelet Aggregation Based on a Benzodiazepinedione Scaffold" *J Am Chem Soc* 116:5077-5083 (1994).

McDowell, R. S. et al., "Structural Studies of Potent Constrained RGD Peptides" *Journal of the American Chemical Society* 114 (24) :9245-9253 (1992).

Olivero et al., "Design, Synthesis and Evaluation of Oral GP IIB/IIIA Antagonists: A Prodrug Approach" *Abstracts of Papers of the American Chemical Society* (Abstract #129; Poster presented at the 212th ACS National Meeting held at Orlando, FL on Aug. 25-29, 1996 is attached.) 212(Pt. 1) (1996).

Packham, M. A., "Role of platelets in thrombosis and hemostasis" *Canadian Journal of Physiology and Pharmacology* 72:278-284 (1994).

Rubas et al., "The Effect of Chemical Modifications on Octanol/Water Partition (Log D) and Permeabilities Across Caco-2 Monolayers" *Adv. Drug Delivery Rev.* 23(1-3) :157-162 (1997).

Saari, W. S. et al., "Cyclization-Activated Prodrugs. Basic Carbamates of 4-Hydroxyanisole" *Journal of Medicinal Chemistry* 33:97-101 (1990).

Sall, D. J. et al., "Platelet Glycoprotein IIb-IIIa Receptor (GpIIb-IIIa) Antagonists Derived from Aminidinoindoles" *Bioorganic & Medicinal Chemistry Letters* 6(1) :81-86 (1996).

Saulnier, M. G. et al., "An Efficient Method for the Synthesis of Guanidino Prodrugs" *Bioorganic & Medicinal Chemistry Letters* 4(16) :1985-1990 (1994).

Sturzebecher, J. et al., "Synthetic Inhibitors of Bovine Factor Xa and Thrombin Comparison of Their Anticoagulant Efficiency" *Thrombosis Research* 54:245-252 (1989).

Verbiscar et al., "Carbamate Ester Latentiation of Physiologically Active Amines" *Journal of Medicinal Chemistry* 13(6) :1176-1179 (1970).

Xue, C-B et al., "Design, Synthesis And In Vitro Activates of a Series of Benzimidazole/Benzoxazole Glycoprotein IIb/IIIa Inhibitors" *Bioorganic & Medicinal Chemistry Letters* 6(3) :339-344 (1996).

IV Administration of Double Prodrugs to Rats (2mg/kg)

X =

Incubation of A (1.5 uM) with Dog Hepatocytes at 37 °C

A: $R_1$= Et, $R_2$ = $Cl_3CCH_2OCO$-
B: $R_1$= H, $R_2$ = H
C: $R_1$= Et, $R_2$ = H
D: $R_1$ = H, $R_2$ = $Cl_3CCH_2OCO$-

| X | Mouse ID$_{50}$ (mg/kg)[a] | |
|---|---|---|
| | Parent = G6249 | G7464 |
| ethoxycarbonyloxymethyl | 0.5 | 0.5 |
| dimethylaminoethoxycarbonyloxy | 18.7 | -- |
| morpholinoethoxycarbonyloxy | 1.4 | -- |
| acetamidoethoxycarbonyloxy | 15 | -- |
| Cl$_3$C-O-C(O)-O- | 2.3 | 0.3 |
| ethylthio-C(O)-O- | 25 | -- |
| phenoxycarbonyloxy | 1.3 | 0.8 |
| 4-fluorophenoxycarbonyloxy | 1.2 | -- |
| acetyloxymethoxycarbonyloxy | 1.1 | -- |
| acetyloxy-CH(CH$_3$)-O-C(O)-O- | 0.3 | 1.4 |
| pivaloyloxy-CH(CH$_3$)-O-C(O)-O- | 1.5 | 0.4 |
| benzoyloxy-CH(CH$_3$)-O-C(O)-O- | | 2.4 |

[a] 1 hour timepoint

US 7,109,326 B2

HALO-ALKOXYCARBONYL PRODRUGS

RELATED APPLICATIONS

This application is a continuation application filed under 37 CFR 1.53(b)(1), claiming priority under 35 USC § 120 to application Ser. No. 10/290,793, filed Nov. 8, 2002, now abandoned and application Ser. No. 09/059,808, filed Apr. 14, 1998, now abandoned and under 35 USC § 119(e) to provisional application Ser. No. 60/042,228, filed Apr. 15, 1997, the contents of which are incorporated herein by reference.

FIELD OF THE INVENTION

This invention relates to novel halo-alkoxycarbonyl derivatives as bioconvertable prodrug moieties for pharmaceutical agents containing a polar or basic functionality. The invention also relates to novel pharmaceutical compositions containing a prodrug comprising the novel prodrug moieties as a component, as well as to processes for producing the prodrugs. The invention further relates to methods for using the novel pharmaceutical compositions described herein.

DESCRIPTION OF RELATED DISCLOSURES

A number of pharmaceutical agents including glycoprotein IIb/IIIa antagonists [International Publication Number 95/04057; Bondinell et al., (1994) Bioorganic & Medicinal Chem., 2(9):897–908; Cook et al., (1993) Thrombosis and Haemostasis, 70(3):531–539; Frederick et al., (1996) Circulation 93(1):129–134; Cox et al., (1996) Thrombosis and Haemostasis 75(3):503–509; Aoki et al., (1996) Throm. Res. 81(4):439–450; Carteuax et al., Throm. and Haem. 70(5): 817–821; International Publication Number WO 95/14682; Hodohara et al., (1995) Pathophysiol. 2:145–151; Sail et al., (1996) Bioorganic and Medicinal Chem. Letts. 6(1):81–86; Xue et al., (1996) Bioorganic and Medicinal Chem. Letts. 6(3):339–344; Colin et al., (1994) J. Med. Chem. 37:3882–3885; Bovy et al., (1994) Bioorg. and Med. Chem. 2(9):881–895], factor Xa inhibitors [Stürzebecher et al., (1989) Thromb. Res. 54:245–252; Hara et al., (1994) Thromb. and Haem. 71(3)314–319], tissue factor-Factor VIIa, trypsin and thrombin inhibitors [U.S. Pat. No. 5,599,793; Bertrand et al., (1996) 35:3147–3155; International Publication Number WO 95/35312; International Publication Number WO 96/24609; International Publication Number WO95/13274; Dickneite et al., (1995) Thromb. Res. 77(4):357–368; Mack et al., (1995) J. Enzyme Inhibition 9:73–86] possess a polar or basic functional group which is integrally responsible for the desired biological activity. For example, structurally related receptors such as integrins recognize the amino acid sequence Arg-Gly-Asp known to be expressed in the extracellular surface glycoprotein GPIIb/IIIa of platelets, endothelial cells, leukocytes, lymphocytes, monocytes and granulocytes. Pharmaceutical agents having the amino acid sequence Arg-Gly-Asp, chemically modified derivatives thereof or non-peptidal analogs, having a polar or basic functionality, compete with intracellular adhesive factors to limit or prevent a key step in the aggregatory cascade. Numerous linear or cyclic peptide derivatives containing the Arg-Gly-Asp sequence or mimics thereof have been described (see references supra; Pierschbacher and Ruoslahti,(1987) J. Biol. Chem. 262:17294; European Patent Application No. 89910207).

In the case of many of the pharmaceutical agents this polar functional group is a nitrogen atom of, for example, a guanidine, alkyl-amidine or aryl-amidine group. This is in part due to these functionalities being good peptidomimetics for the guanidine group of arginine, an important amino acid residue found in many of the natural ligands and substrates of the indicated proteins and enzymes. Because these functionalities are highly basic (for example, $pK_a$ of the conjugate acid $\geq 11$), they remain protonated at physiologically relevant pH's. The ionic nature of such protonated species hinders their permeability across lipophilic membranes which can reduce bioavailability when the pharmaceutical agent is administered orally.

In order to circumvent such a problem, it is often advantageous to perform a derivatization or chemical modification of the polar functionality such that the pharmaceutical agent becomes neutrally charged and more lipophilic thereby facilitating absorption of the drug. However, for the derivatization of such a polar functionality to be useful, the derivatization must be bioconvertable at the target site or sites of desired pharmacological activity and cleaved under normal physiological conditions to yield the biologically active drug. The term "prodrug" has been used to denote such a chemically modified intermediate.

The alkoxycarbonyl (carbamoyl) and acyloxymethyl carbamate groups have been investigated as prodrug moieties capable of producing a bioconvertable prodrug of amine and amidine nitrogens (for example, Saulnier, et al. (1994) Bioorg. Med. Chem. Letts. 4(16):1985–1990). Lower alkoxycarbonyl groups such as methoxycarbonyl and ethoxycarbonyl, optionally substituted phenoxycarbonyl groups, groups such as benzyloxycarbonyl and p-methoxybenzyloxycarbonyl and amide oximes have been described as prodrug moieties for these functional groups (for example, European Patent Application No. 0743320).

While the carbamoyl group has many of the desired characteristics to be utilized as a prodrug moiety, it suffers from the disadvantage that the group is not readily bioconvertable. Alkoxycarbonylamines cleave too slowly in plasma and upon systemic circulation to the respective amine to be of practical importance. This is partly due to the fact that mammals possess no carbamoyl specific hydrolases. Cholinesterases have been shown to slowly hydrolyze some carbamates, however the cleavage is slow and the cleaving enzyme is reversibly inhibited by the cleavage resulting in a further reduction in the rate of hydrolysis (Alexander et al., (1988) J. Med. Chem. 31:318–322).

It would be highly desirable to have a modified alkoxycarbonyl-based prodrug moiety for N-containing polar functional groups which possess all of the desirable characteristics associated with a prodrug moiety and cleave readily once in the bloodstream to liberate the free N-containing drug.

SUMMARY OF THE INVENTION

The present invention provides modified alkoxycarbonyl groups as bioconvertable prodrug moieties for pharmaceutical agents, drugs or medicaments having a polar or basic functional group. It is a feature of the present invention that when administered to animals including humans the pharmaceutical compositions comprising the novel prodrugs are more bioavailable following non-systemic administration than the parent pharmaceutical agents or drugs from which they are derived. Thus, the novel prodrugs which comprise the prodrug moiety of the present invention may be used wherever the parent drug or pharmaceutical agent is used and advantageously provide increased biomembrane transport and improved bioavailability from the gastrointestinal tract, rectum, skin and the eyes. The prodrugs of the invention can be incorporated into unit dosage forms such as tablets and capsules for oral delivery, as well as into suspensions, ointments and the like, depending on the particular drug or medicament and its target area.

In particular embodiments, the present invention provides such prodrug forms of pharmaceutical agents which following administration cleave in a therapeutically useful time frame and in such a manner as to enable the original parent composition to be released at its therapeutic site or sites of activity and to further permit the cleaved prodrug moiety to be metabolized in a nontoxic fashion.

According to a particular aspect of the invention the pharmaceutical composition comprising the prodrug moiety of the present invention can be described by the following formula:

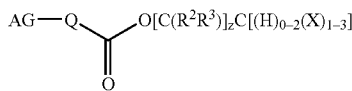

wherein $[(H)_{0-2}(X)_{1-3}]$ is selected from the group consisting of $X_3$, $HX_2$, and $H_2X$ and X is a halogen selected from the group consisting of F, Cl, Br, I or a combination thereof; $R^2$ and $R^3$ are the same or different and are selected from the group consisting of H, $C_1$–$C_4$alkyl, $C_1$–$C_4$alkoxy, cyano and halo(F, Cl, Br, I)$C_1$–$C_4$alkyl, z is an integer from 1 to 5, and AG-Q is a biologically active pharmaceutical agent wherein Q is a basic N-containing functionality selected from the group consisting of an amino, amidino, aminoalkyleneamino, iminoalkyleneamino, and guanidino group. According to this aspect of the invention the prodrug moiety, —COO$[C(R^2R^3)]_zC[(H)_{0-2}(X)_{1-3}]$ is linked to the N containing functionality via an N atom.

According to a preferred aspect of the present invention, halo-alkoxycarbonyl moieties, for example, 2,2,2-tri-halo-ethoxycarbonyl moities are provided as bioconvertable prodrug moieties for polar or basic functionalities in pharmaceutical agents, drugs or medicaments. Preferred polar or basic functionalities, represented by Q or B-Q herein, are N-containing functionalities having a $pK_a$ of the conjugate acid sufficiently high that the N-containing group is at least 10% positively charged at physiological pH. Exemplary N-containing functional groups, Q, are primary and secondary amino, amidino, aminoalkyleneamino, iminoalkyleneamino, and guanidino groups. Especially preferred are the guanidino and amidino groups and B-Q groups such as the alkyl-, alkenyl, alkynyl, substituted or unsubstituted aryl, arylalkyl, heterocyclic or heteroaromatic such as substituted or unsubstituted phenyl-, napthyl-, and pyridyl-amidino groups.

In a preferred aspect, the prodrug moiety is a 2,2,2,-trichloroethoxycarbonyl group. According to this aspect of the present invention, the prodrug moiety can be represented by the following structure:

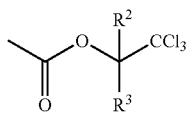

wherein the carbonyl group:

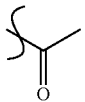

is linked to a pharmaceutical agent comprising at least one polar or basic N-containing group via the N atom.

In a preferred aspect of the present invention, the prodrug moiety can be represented by P or P' and the pharmaceutical agent can be represented by AG-Q with Q representing an N-containing functionality of the parent agent. According to a particular embodiment, Q is an amidino group and the prodrug of the present invention is represented by the following two tautomeric structures:

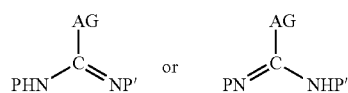

wherein AG represents a parent pharmaceutical agent substructure and wherein P and P' are the same or different and are independently selected from H or a 2,2,2,-tri-halo-ethoxycarbonyl moiety, at least one of P or P' being a 2,2,2-tri-halo-ethoxycarbonyl moiety where the ethoxycarbonyl group is linked to the N-containing functionality via the carbonyl group. According to this aspect of the invention, the ethoxy group is —OCH$_2$CX$_3$, —OCHR$^2$CX$_3$, or —OCR$^2$R$^3$CX$_3$, R$^2$ and R$^3$ being defined herein, and preferably being H.

According to a further aspect of the present invention, Q is B-Q and the pharmaceutical agent can be represented by AG-B-Q wherein B is an substituted or unsubstituted alkyl, alkenyl or alkynyl, a substituted or unsubstituted aryl, arylalkyl, heterocyclic, or heteroaromatic. In preferred embodiments B is a unsubstituted or substituted phenyl, napthyl or pyridyl. As an example of this aspect of the present invention, Q is an amidino group and the prodrug is represented by the following two tautomeric structures:

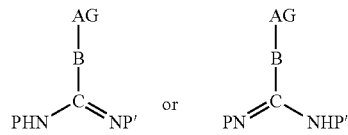

wherein AG represents a parent pharmaceutical agent substructure and wherein P and P' are the same or different and are independently selected from H or a 2,2,2-trichloroethoxycarbonyl moiety, at least one of P or P' being a 2,2,2-trichloroethoxycarbonyl moiety where the ethoxycarbonyl group is linked to the N-containing functionality via the carbonyl group. B is preferably an unsubstituted or substituted aryl or arylalkyl such as phenyl, napthyl or pyridyl. According to this aspect of the invention, the ethoxy group is —OCH$_2$CCl$_3$, —OCHR$^2$CCl$_3$, or —OCR$^2$R$^3$CCl$_3$, R$^2$ and R$^3$ being defined herein and preferably being H.

The invention further provides novel compositions comprising the prodrugs of the present invention as well as methods of making and employing the novel prodrugs. The pharmaceutical compositions comprising the prodrugs of the present invention include all stereoisomers and pharmaceutically acceptable salts of the novel compositions.

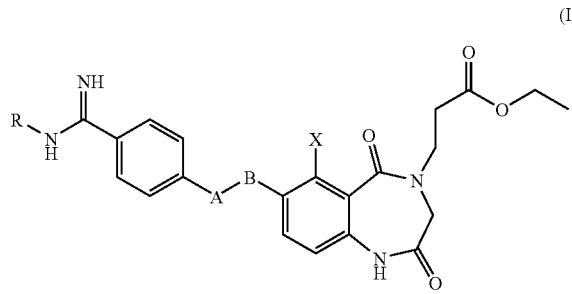

(I)

in rats after oral administration. Aryloxycarbonylamidines and acyloxy-alky-carbonylamidines are more physiologically labile than 2,2,2-trichloroethoxycarbonyl amidines (entries 6 and 7 of FIG. 2 and entries 4 and 5 of FIG. 3) but such chemical modifications do not significantly increase oral bioavailability in rats. The 2,2,2-trichloroethoxycarbonyl prodrug exhibits the proper balance of lability and stability.

Figure 6:
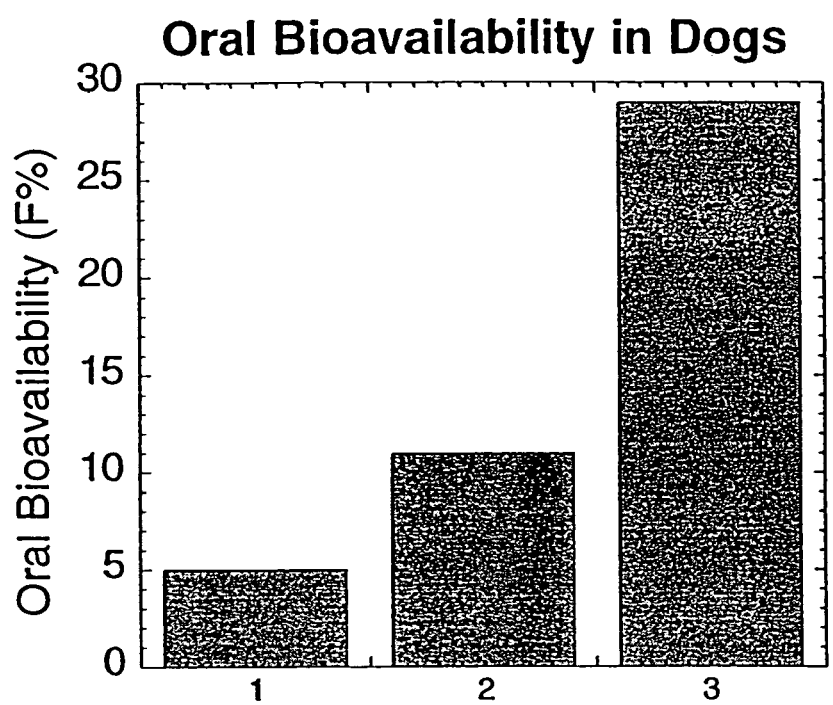

FIG. 6 graphically depicts bioavailability of various prodrugs in dogs after oral administration. Use of the 2,2,2-trichloroethoxycarbonyl prodrug moiety doubled the oral bioavailability of compounds of the general structure (I) relative to the ethoxycarbonyl derivative when administereed orally at comparable doses to dogs. At lower doses the oral bioavailability increased to 29%.

Figure 7:
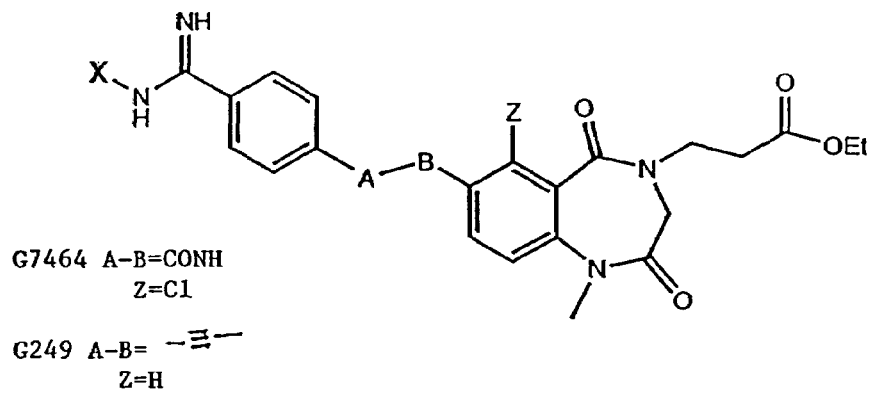

FIG. 7 show the results of oral bioavailability assessed by dosing mice at 100 mg/kg orally and sacrificing the mice at either 1 or 3 hour timepoints. The mice were exsanguinated and ex vivo platelet aggregation measured by $ID_{50}$.

DETAILED DESCRIPTION OF THE PREFERRED EMBODIMENTS

Definitions

The terms "pharmaceutical agent," "drug," "medicament" and the like are used interchangeably herein with the term "parent compound" or "parent drug" to refer to a compound, having pharmacological activity. Pharmaceutical agents or parent compounds characteristically contain at least one polar or basic nitrogen-(N—) containing functionality. It is characteristic that the pharmaceutical agent comprising at least one N-containing functionality have a $pK_a$ of the conjugate acid sufficiently high so that the functionalities are at least 10% positively charged at physiological pH. Functionalities that are positively charged are associated with an H ion at physiological pH. In various aspects of the present invention the pharmaceutical agent or parent drug is represented by the shorthand notation AG-Q or AG-B-Q. In this shorthand notation, AG is conveniently used in place of the parent drug "substructure" with Q, or B-Q representing the parent drug at least one polar or basic N-containing functionality as defined herein, B further defining the parent drug substructure. For example, in one embodiment, the parent drug is an amidine containing GPIIb/IIIa antagonist such as those described in International Publication No. WO 93/08174 and U.S. Pat. No. 5,565,449. In this example AG would represent the parent substructure and the polar or basic N-containing functionality, e.g., an amidino group, —C(=NH)—$NH_2$, is conveniently described in shorthand notation by Q. As a further example, AG may contain a substituted or unsubstituted aryl or arylalkyl-amidino group represented by —B-Q.

The pharmaceutical agent is pharmaceutically active or "bioactive," by virtue of possessing a biological activity such as inhibiting platelet aggregation in the absence of the prodrug moiety of the present invention. As noted above, it is a characteristic of the pharmaceutical agent of the present invention that it contain at least one polar or basic N-containing functionality (Q) as herein defined.

The term "basic" as used in the context of the present invention refers to a funtionality or moiety having a positive charge due to association with H ion at physiological pH.

The term "polar" as used herein refers to funtionalities or moieties not charged at physiological pH, but possess a dipole moment in an aqueous (non-lipid) environment.

"Bioavailable" as used herein means that at least some amount of the parent drug is present in the systemic circulation. Formal calculations of oral bioavailability are described in terms of an F value ("Fundamentals of Clinical Pharmacokinetics," John G. Wegner, Drug Intelligence Publications; Hamilton, Ill. 1975). F values are derived from the ratio of the concentration of the parent drug in the systemic circulation (e.g., plasma) following intravenous administration to the concentration of the parent drug in the systemic circulation after administration by a non-intravenous route (e.g., oral). Therefore, oral bioavailability within the scope of the present invention contemplates the ratio or F value of the amount of parent drug detectable in the plasma after oral administration compared to intravenous administration.

"Pharmaceutically acceptable salts" include both acid and base addition salts.

The term "prodrug" is used herein to refer to a derivative of a parent drug that has enhanced pharmaceutically desirable characteristics or properties (e.g. transport, bioavailablity, pharmacodynamics, etc.) and requires "bioconversion," i.e., cleavage of the "prodrug moiety" either spontaneously or enzymatically, within the organism to release the active parent drug.

The term "alkyl" or the prefix "alk" mean a branched or unbranched, saturated aliphatic hydrocarbon radical, having the number of carbon atoms specified, or if no number is specified, having up to about 12 carbon atoms. Examples of alkyl radicals include methyl, ethyl, n-propyl, isopropyl, n-butyl, iso-butyl, sec-butyl, tert-butyl, n-pentyl, 2-methylbutyl, 2,2-dimethylpropyl, n-hexyl, 2-methylpentyl, 2,2-dimethylbutyl, n-heptyl, 2-methylhexyl, and the like. The terms "lower alkyl" "$C_1$–$C_6$ alkyl" and "alkyl of 1 to 6 carbon atoms" are synonymous and used interchangeably. A preferred "$C_1$–$C_6$ alkyl" group is ethyl.

Substituted alkyl groups include those that are substituted by one, two or three halogen, hydroxy, amino, carboxy, acyloxy (substituents such as formyloxy, acetoxy, proprionyloxy, butryloxy, pentanoyloxy and the like,) carbamoyl, carbamoyloxy, cyano, morpholino, or methylsulfonylamino substituents and the like.

Examples of the above substituted alkyl groups include but are not limited to, hydroxyethyl, 2-morpholinoethyl, 6-hydroxyhexyl, 2,4-dichloro(n-butyl), 2-amino(iso-propyl), 2-carbamoyloxyethyl and the like.

The term "alkenyl" means a branched or unbranched hydrocarbon radical having the number of carbon atoms designated containing one or more carbon-carbon double bonds, each double bond being independently cis, trans, or a nongeometric isomer.

The term "alkynyl" means a branched or unbranched hydrocarbon radical having the number of carbon atoms designated containing one or more carbon-carbon triple bonds.

The terms "alkoxy" or "$C_1$–$C_{12}$ alkoxy" and the like are used interchangeably herein and denote groups such as methoxy, ethoxy, n-propoxy, isopropoxy, n-butoxy, t-butoxy and like groups. Substituted alkoxy groups include those that are substituted by one, two or three halogen, hydroxy, amino, carboxy, acyloxy (substituents such as formyloxy, acetoxy, proprionyloxy, butryloxy, pentanoyloxy and the like,) carbamoyl, carbamoyloxy, cyano, morpholino, or methylsulfonylamino substituents and the like.

The term "aryl" when used alone means a homocyclic or polycyclic aromatic radical, whether or not fused, having the number of carbon atoms designated. Preferred aryl groups include phenyl, napthyl, biphenyl, phenanthrenyl, napthacenyl, and the like (see e.g. Lang's Handbook of Chemistry (Dean, J. A., ed) 13th ed. (1985) Table 7-2).

The term "substituted phenyl" or "substituted aryl" denotes a phenyl group or aryl group substituted with one, two or three substituents chosen from halogen(F, Cl, Br, I), hydroxy, protected hydroxy, cyano, nitro, $C_1$–$C_6$ alkyl, $C_1$–$C_6$ alkoxy, carboxy, protected carboxy, carboxymethyl, protected carboxymethyl, hydroxymethyl, protected hydroxymethyl, aminomethyl, protected aminomethyl, trifluoromethyl N-(methylsulfonylamino) or other groups specified.

Examples of the term "substituted phenyl" includes but are not limited to a mono- or di(halo)phenyl group such as 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro-4-fluorophenyl, 2-fluorophenyl and the like; a mono- or di(hydroxy)phenyl group such as 4-hydroxyphenyl, 3-hydroxyphenyl, 2,4-dihydroxyphenyl, the protected-hydroxy derivatives thereof and the like; a nitrophenyl group such as 3- or 4-nitrophenyl; a cyanophenyl group, for example, 4-cyanophenyl; a mono- or di(lower alkyl)phenyl group such as 4-methylphenyl, 2,4-dimethylphenyl, 2-methylphenyl, 4-(isopropyl)phenyl, 4-ethylphenyl, 3-(n-propyl)phenyl and the like; a mono- or di(alkoxy)phenyl group, for example, 2,6-dimethoxyphenyl, 4-methoxyphenyl, 3-ethoxyphenyl, 4-(isopropoxy)phenyl, 4-(t-butoxy)phenyl, 3-ethoxy-4-methoxyphenyl and the like; 3- or 4-trifluoromethylphenyl; a mono- or dicarboxyphenyl or (protected carboxy)phenyl group such 4-carboxyphenyl; a mono- or di(hydroxymethyl)phenyl or (protected hydroxymethyl)phenyl such as 3-(protected hydroxymethyl)phenyl or 3,4-di(hydroxymethyl)phenyl; a mono- or di(aminomethyl)phenyl or (protected aminomethyl)phenyl such as 2-(aminomethyl)phenyl or 2,4-(protected aminomethyl)phenyl; or a mono- or di(N-(methylsulfonylamino))phenyl such as 3-(N-methylsulfonylamino))-phenyl. Also, the term "substituted phenyl" represents disubstituted phenyl groups wherein the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl and the like. Preferred substituted phenyl groups include the 2- and 3-trifluoromethylphenyl, the 4-hydroxyphenyl, the 2-aminomethylphenyl and the 3-(N-(methylsulfonylamino))phenyl groups.

The term "arylalkyl" or "aralkyl" means one, two, or three aryl groups having the number of carbon atoms designated, appended to an alkyl radical having the number of carbon atoms designated including but not limited to; benzyl, napthylmethyl, phenethyl, benzhydryl (diphenylmethyl), trityl, and the like. A preferred arylalkyl group is the benzyl group.

The term "substituted $C_6$–$C_{10}$aryl-$C_1$–$C_8$alkyl" denotes a $C_1$–$C_8$alkyl group substituted at any carbon with a $C_6$–$C_{10}$aryl group bonded to the alkyl group through any aryl ring position and substituted on the $C_1$–$C_8$alkyl portion with one, two or three groups chosen from halogen (F, Cl, Br, I), hydroxy, protected hydroxy, amino, protected amino, $C_1$–$C_7$acyloxy, nitro, carboxy, protected carboxy, carbamoyl, carbamoyloxy, cyano, $C_1$–$C_6$alkylthio, N-(methylsulfonylamino) or $C_1$–$C_4$alkoxy. Optionally the aryl group may be substituted with one, two, or three groups chosen from halogen, hydroxy, protected hydroxy, nitro, $C_1$–$C_6$alkyl, $C_1$–$C_4$alkoxy, carboxy, protected carboxy, carboxymethyl, protected carboxymethyl, hydroxymethyl, protected hydroxymethyl, aminomethyl, protected aminomethyl, or an N-(methylsulfonylamino) group. As before, when either the $C_1$–$C_8$alkyl portion or the aryl portion or both are disubstituted, the substituents can be the same or different.

Examples of the term "substituted $C_6$–$C_{10}$aryl$C_1$–$C_8$alkyl" include groups such as 2-phenyl-1-chloroethyl, 2-(4-methoxyphenyl)ethyl, 2,6-dihydroxy-4-phenyl(n-hexyl), 5-cyano-3-methoxy-2-phenyl(n-pentyl), 3-(2,6-dimethylphenyl)n-propyl, 4-chloro-3-aminobenzyl, 6-(4-methoxyphenyl)-3-carboxy(n-hexyl), 5-(4-aminomethyl phenyl)-3-(aminomethyl)(n-pentyl), and the like.

The term "carboxy-protecting group" as used herein refers to one of the ester derivatives of the carboxylic acid group commonly employed to block or protect the carboxylic acid group while reactions are carried out on other functional groups on the compound. Examples of such carboxylic acid protecting groups include 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxybenzhydryl, 2,2',4,4'-tetramethoxybenzhydryl, t-butyl, t-amyl, trityl,4-methoxytrityl, 4,4'-dimethoxytrityl, 4,4',4''-trimethoxytrityl, 2-phenylprop-2-yl, trimethylsilyl, t-butyldimethylsilyl, phenacyl, 2,2,2-trichloroethyl, β-(trimethylsilyl)ethyl, β-(di(n-butyl)methylsilyl)ethyl, p-toluenesulfonylethyl, 4-nitrobenzylsulfonylethyl, allyl, cinnamyl, 1-(trimethylsilylmethyl)prop-1-en-3-yl, and like moieties. Further examples of these groups are found in E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981, Chapter 5. The term "protected carboxy" refers to a carboxy group substituted with one of the above carboxy-protecting groups.

As used herein the term "amide-protecting group" refers to any group typically used in the peptide art for protecting the peptide nitrogens from undesirable side reactions. Such groups include p-methoxyphenyl, 3,4-dimethoxybenzyl, benzyl, O-nitrobenzyl, di-(p-methoxyphenyl)methyl, triphenylmethyl, (p-methoxyphenyl)diphenylmethyl, diphenyl-4-pyridylmethyl, m-2-(picolyl)-N'-oxide, 5-dibenzosuberyl, trimethylsilyl, t-butyl dimethylsilyl, and the like. Further descriptions of these protecting groups can be found in "Protective Groups in Organic Synthesis", by Theodora W. Greene, 1981, John Wiley and Sons, New York.

Unless otherwise specified, the terms "heterocyclic group" or "heterocyclic" or "HET" or "heterocyclyl" are used interchangeably herein and refer to any mono-, bi-, or tricyclic saturated, unsaturated, or aromatic ring having the number of atoms designated where at least one ring is a 5-, 6- or 7-membered ring containing from one to four heteroatoms selected from nitrogen, oxygen, and sulfur. Preferably at least one heteroatom is nitrogen (Lang's Handbook of Chemistry, supra). Typically, the 5-membered ring has 0 to 2 double bonds and the 6- or 7-membered ring has 0 to 3 double bonds and the nitrogen or sulfur heteroatoms may optionally be oxidized, and any nitrogen heteroatom may optionally be quaternized. Included in the definition are any bicyclic groups where any of the above heterocyclic rings are fused to a benzene ring. Heterocyclics in which nitrogen is the heteroatom are preferred.

MODES FOR CARRYING OUT THE INVENTION

This invention provides novel prodrugs which are mono-, di-, or tri-halo-, preferably tri-halo-alkoxycarbonyl derivatives, such as trichloroalkoxycarbonyl derivatives of pharmaceutical agents, drugs or medicaments. According to the present invention, a pharmaceutical agent, as described herein, is substituted according to, for example, the methods provided herein, to contain at least one novel prodrug moiety.

The halo-alkoxycarbonyl prodrug moieties of the present invention produce a derivative or prodrug of the parent compound which facilitates absorption by masking the ionic charge of the nitrogen containing functionality of the parent compound. Advantageously, the prodrug moiety is sufficiently stable to survive premature cleavage in the stomach, intestines, and non-target sites. The prodrug moiety, is readily cleaved at the target site (e.g. the systemic circulation for most cardiovascular-based drugs) in a biologically relevant time frame and in high efficiency.

Suitable halo-alkoxycarbonyl prodrug moieties such as the trichloroalkoxycarbonyl moieties of the present invention produce by-products after metabolic cleavage of the prodrug moiety from the parent drug that are safe, non-toxic, and easily cleared by the system. In preferred embodiments, the by products are $CO_2$ and an alcohol, preferably 2,2,2-trichloroethanol an agent present in drinking water as a by product of the chlorination process (Bercz et al., (1991) J. Am. Tox. 10(2):223–232). Preferably the mechanism of prodrug cleavage does not have undesired detrimental biological repercussions (i.e. have an inhibitory effect on prodrug cleaving enzyme(s), etc.). Advantageously the prodrug moiety is easily and economically prepared.

The present invention is meant to encompass mono-, di-, and tri- halo-, and preferably, tri-halo-alkoxycarbonyl prodrug derivatives as bioconvertable prodrug moieties. By halo-alkoxycarbonyl prodrug moiety is meant a compound of general formula:

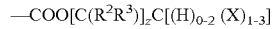

wherein $[(H)_{0-2}(X)_{1-3}]$ is selected from the group consisting of $X_3$, $HX_2$, and $H_2X$ and X is a halogen selected from the group consisting of F, Cl, Br, I or a combination thereof. Preferably the halogen is flourine or chlorine or a combination thereof and more preferably the halogen is chlorine. Preferred among the mono, di and tri-chloroalkoxycarbonyl groups are the trichloroalkoxycarbonyl groups.

Preferred among the halo-alkoxycarbonyl prodrug moieties of the present invention are straight chain or branched chain substituted or saturated aliphatic $C_2$ to $C_6$ alkyoxycarbonyl groups. Therefore in the foregoing formula, the subscript z is preferably 2–5. Preferred among the branched and straight chain alkoxycarbonyl groups are the straight chain substituted or saturated aliphatic groups. Preferred among the straight chain groups are the $C_2$–$C_6$ substituted and saturated aliphatic groups and especially the saturated and substituted 2,2,2-trichloroethoxycarbonyl prodrug moieties.

Therefore in a preferred embodiment the invention provides prodrugs moieties of the following structural formula:

The prodrug moiety —COO(CR²R³)CCl₃ 1) produces a neutrally charged prodrug derivative of the parent compound which increases permeability across lipophilic membranes, 2) can be easily and economically prepared from precursor alkyl chloroformates, 3) results in ethoxycarbonyl derivatives stable to pre-systemic cleavage and 4) the resulting by products of systemic cleavage are $CO_2$ and an alcohol.

In the above formula the ethoxy group is —O(R²R³C)—, wherein $R^2$ and $R^3$ are the same or different and represent hydrogen, $C_1$–$C_4$alkoxy, $C_1$–$C_4$alkyl, cyano, and halo(F, Cl, Br, I)$C_1$–$C_4$alkyl, (ii) optionally substituted $C_1$–$C_{12}$alkyl, (iii) optionally substituted $C_3$–$C_7$alkenyl, (iv) optionally substituted $C_3$–$C_7$alkynyl, (v) optionally substituted $C_3$–$C_{12}$cycloalkyl, (vi) optionally substituted $C_5$–$C_{12}$cycloalkenyl, (vii) optionally substituted $C_6$–$C_{14}$aryl, (viii) optionally substituted $C_1$–$C_6$alkyl$C_6$–$C_{14}$aryl, (ix) optionally substituted $C_3$–$C_6$alkenyl-$C_6$–$C_{10}$aryl, (x) optionally substituted heterocyclyl, (xi) optionally substituted $C_1$–$C_6$alkyl-heterocyclyl, (xii) optionally substituted $C_1$–$C_8$alkoxy, (xiii) optionally substituted $C_1$–$C_8$alkoxycarbonyl, (xiv) optionally substituted $C_1$–$C_8$thioalkoxy, (xv) optionally substituted $C_3$–$C_{10}$alkenoxy, and (xvi) optionally substituted $C_6$–$C_{14}$aryloxy, (xvii) optionally substituted $C_6$–$C_{14}$aryloxycarbonyl, (xviii) optionally substituted $C_6$–$C_{14}$aryl$C_1$–$C_6$alkyloxycarbonyl, where the substituents are usually one to three $R^2$ groups.

Preferred among the 2,2,2-trichloroethoxycarbonyl prodrug moieties of the present invention are the 2,2,2-trichloroethoxycarbonyl moieties wherein the ethoxy group —OCR$^2$R$^3$—, R$^2$ and R$^3$ are the same or different and represent hydrogen, $C_1$–$C_4$alkoxy, $C_1$–$C_4$alkyl, cyano, and halo(F, Cl, Br, I)$C_1$–$C_4$alkyl. Preferably R$^2$ and R$^3$ are methyl or H or a combination thereof. Preferred among these moieties is the —HR$^2$CO— moiety. Most preferred among the 2,2,2-trichloroethoxycarbonyl groups is —COOCH$_2$CCl$_3$.

The pharmaceutical agents are pharmaceutically active compounds comprising at least one polar or basic nitrogen-containing functionality Q. Preferred pharmaceutical agents have an N-containing functionality, Q, having a pK$_a$ of the conjugate acid sufficiently high so that the molecules are at least 10% positively charged (associated with an H ion) at physiological pH. Suitable parent pharmaceutical compounds comprise at least one Q group. Q may be, for example (1) a primary, or secondary, amine or imine, (2) an amidino (aminoiminomethyl) group, (3) an aminoalkyleneamino group, (4) an iminoalkyleneamino group or (5) a guanidino group. According to this aspect of the present invention the parent compound contains at least one amino group including;

—NH$_2$,

—NR$^4$H, 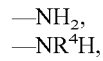

where R$^4$ is typically, but not limited to; (i) an optionally substituted radical selected from (a) —NR$^7$R$^8$, (b) —C(=NR$^9$)—NR$^7$R$^8$, (c) —N=CR$^{10}$—NR$^7$R$^8$, (d) —NR$^{11}$—CR$^{10}$=NR$^9$, and (e) —NR$^{11}$—C(=NR$^9$)—NR$^7$R$^8$ where each R$^7$, R$^8$, R$^9$, R$^{10}$, and R$^{11}$ is independently selected from hydrogen, hydroxy, $C_1$–$C_4$alkoxy, $C_1$–$C_4$alkyl, cyano, and halo(F, Cl, Br, I)$C_1$–$C_4$alkyl, (ii) optionally substituted $C_1$–$C_{12}$alkyl, (iii) optionally substituted $C_3$–$C_7$alkenyl, (iv) optionally substituted $C_3$–$C_7$alkynyl, (v) optionally substituted $C_3$–$C_{12}$cycloalkyl, (vi) optionally substituted $C_5$–$C_{12}$cycloalkenyl, (vii) optionally substituted $C_6$–$C_{14}$aryl, (viii) optionally substituted $C_1$–$C_6$alkyl$C_6$–$C_{14}$aryl, (ix) optionally substituted $C_3$–$C_6$alkenyl-$C_6$–$C_{10}$aryl, (x) optionally substituted heterocyclyl, (xi) optionally substituted $C_1$–$C_6$alkyl-heterocyclyl, (xii) optionally substituted $C_1$–$C_8$alkoxy, (xiii) optionally substituted $C_1$–$C_8$alkoxycarbonyl, (xiv) optionally substituted $C_1$–$C_8$thioalkoxy, (xv) optionally substituted $C_3$–$C_{10}$alkenoxy, and (xvi) optionally substituted $C_6$–$C_{14}$aryloxy, (xvii) optionally substituted $C_6$–$C_{14}$aryloxycarbonyl, (xviii) optionally substituted $C_6$–$C_{14}$aryl$C_1$–$C_6$alkyloxycarbonyl, where the substituents are usually one to three R$^{12}$, each R$^{12}$ typically selected from (a) optionally substituted $C_6$–$C_{12}$aryloxy, (b) optionally substituted $C_6$–$C_{12}$arylamino, (c) optionally substituted $C_6$–$C_{12}$aroyl, (d) optionally substituted $C_6$–$C_{12}$arylthio, where the substituents are usually one to three R$^{13}$, each R$^{13}$ typically selected from nitro, amino, $C_1$–$C_8$alkylamino, di-($C_1$–$C_8$)alkylamino, amidino, aminomethyleneimino, imino, imino-$C_1$–$C_4$alkyl, iminomethyleneamino, guanidino, $C_6$–$C_{10}$arylamino, $C_1$–$C_8$acylamino, $C_1$–$C_4$alkylsulfonamino, azido, cyano, hydroxy, hydroxy$C_1$–$C_8$alkyl, $C_1$–$C_8$alkoxy, phenyloxy, $C_1$–$C_8$alkanoyloxy, $C_1$–$C_8$alkanoyl, $C_6$–$C_{12}$aroyl, benza-mido, phenyl, halo(F, Cl, Br, I), halo$C_1$–$C_8$-alkyl, and $C_1$–$C_8$alkyl, (e) $C_1$–$C_8$alkoxy (f) $C_1$–$C_8$alkthio (g) halo(F, Cl, Br, I), (h) hydroxy, (i) mercapto, (j) $C_1$–$C_8$alkylcarbonyl, (k) carbamoyl, (l) formyl, (m) formyloxy, (n) carboxy, (o) carb-$C_1$–$C_8$alkyloxy, (p) $C_1$–$C_8$alkanoyloxy, (q) N-($C_1$–$C_8$) alkylcarboxamido, (r) N-$C_1$–$C_8$), N-($C_1$–$C_8$)dialkylcarboxamido, (s) carbamoyloxy, (t) N-($C_1$–$C_8$)alkylcarbamoyloxy, (u) N-($C_1$–$C_8$), N-($C_1$–$C_8$)dialkylcarbamoyloxy, (v) $C_1$–$C_8$alkylsulfinyl, (w) $C_1$–$C_8$alkylsulfonyl, (x) $C_1$–$C_8$alkylsulfonato, (y) sulfo, (z) sulfonamido, (aa) N-($C_1$–$C_8$)alkylsulfonamido, (ab) N-($C_1$–$C_8$), N-($C_1$–$C_8$)dialkylsulfonamido, (ac) amino, (ad) $C_1$–$C_8$alkylamino, (ae) $C_1$–$C_8$ dialkylamino, (af) $C_1$–$C_8$ acylamino, (ag) N-($C_1$–$C_8$), N-($C_1$–$C_8$)-diacylamino, (ah) N-($C_1$–$C_8$)-alkyl-N-($C_1$–$C_8$)-acylamino, (ai) formylamino, (aj) ureido, (ak) isothioureido, (al) amino-$C_2$–$C_8$alkylthio, (am) amino-$C_2$–$C_8$alkloxy, (an) amidino, (ao) guanidino, (ap) aminomethyleneimino, (aq) imino, (ar) imino-$C_1$–$C_4$ alkyl, (as) iminomethyleneamino, (at) glycylamino, (au) glycyl, (av) phthalimido, (aw) succinimido, (ax) morpholino, (ay) $C_1$–$C_8$ alkylsulfonamido, (az) N-($C_1$–$C_8$)-alkyl-N-($C_1$–$C_8$)alkyl sulfonoylamino, (ba) $C_1$–$C_8$alkylsulfinamino, (bb) N-($C_1$–$C_8$)alkyl-N-($C_1$–$C_8$) alkylsulfinamino, (bc) $C_1$–$C_8$ alkoxyamino, (bd) $C_1$–$C_8$ alkoxyamino, (be) N-($C_1$–$C_8$)alkyl-N-($C_1$–$C_8$)alkoxyamino, (bf) $C_3$–$C_7$cycloalkyl, (bg) oxo, and (bh) heterocyclyl, optionally any one or two pairs of R$^4$–R$^{11}$ may independently be joined to form one or two optionally substituted heterocyclic rings, each ring optionally fused with one or two optionally substituted homocyclic or heterocyclic rings of from four to seven atoms where any heterocyclic ring contains from one to four heteroatoms selected from N, O, and S and where any ring may be substituted with from one to three R$^{13}$, either isolated or conjugated with other nitrogen atoms to form groups including but not limited to aminomethyleneimino;

(2) an amidino (aminoiminomethyl) group including;

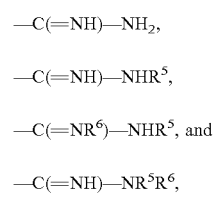

where R$^5$ and R$^6$ are the same or different and are as defined above for R$^4$, 3) an aminoalkyleneamino group including;

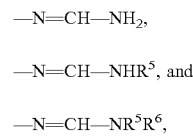

where R$^5$ and R$^6$, are the same or different and are the same as R$^4$ defined above, (4) an iminoalkyleneamino group, including;

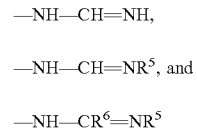

where R$^5$, and R$^6$ are the same or different and are as defined above for R$^4$, (5) a guanidino (aminoiminomethyleneamino) group including;

—NH—C(=NH)—NH$_2$,

—NH—C(=NH)—NR$^5$H,

—NH—C(=NH)—NR$^5$R$^6$,

—NH—C(=NR$^4$)—NR$^5$R$^6$,

—NR$^5$—C(=NH)—NR$^5$R$^6$,

—NR$^5$—C(=NR$^5$)—NH$_2$,

—NR$^5$—C(=NH)—NH$_2$,

—NR$^5$—C(=NR$^5$)—NHR$^6$, and

—NR$^5$—C(=NH)—NHR$^6$, where R$^5$, R$^6$, and R$^4$ are the same or different and are as defined above for R$^4$, Preferably the parent agent contains at least one amidino (aminoiminomethyl) group including;

—C(=NH)—NH$_2$,

—C(=NH)—NHR$^5$,

—C(=NR$^6$)—NHR$^5$,

—C(=NH)—NR$^5$R$^6$, and

—C(=NR$^4$)—NR$^5$R$^6$, where R$^5$, R$^6$, and R$^4$ are defined above, an iminoalkyleneamino group, including;

—NH—CH=NH,

—NH—CH=NR$^5$,

—NH—CR$^6$=NR$^5$, and

—NR$^4$—CR$^6$=NR, where R$^5$, R$^6$, and R$^4$ are defined above, and guanidino groups including;

—NH—C(=NH)—NH$_2$,

—NH—C(=NH)—NR$^5$H,

—NH—C(=NH)—NR$^5$R$^6$,

—NH—C(=NR$^4$)—NR$^5$R$^6$,

—NR$^5$—C(=NH)—NR$^5$R$^6$,

—NR$^5$—C(=NR$^5$)—NH$_2$,

—NR$^5$—C(=NH)—NH$_2$,

—NR$^5$—C(=NR$^5$)—NHR$^6$, and

—NR$^5$—C(=NH)—NHR$^6$, where R$^5$, R$^6$, and R$^4$ are defined above, and multiples thereof.

In preferred embodiments Q is B-Q such as amidino (H$_2$NC(=NH)—B), guanidino (H$_2$N-C(=NH)—NH—B), and amino, H$_2$N-B or HNR$^4$B or an imino (NH$_2$=CHNH—B) as indicated above wherein B is a substituted or unsubstituted straight or branched chain alkyl, alkenyl or alkynyl, a substituted or unsubstituted aryl, or alkylaryl, heterocyclic, or heteroaromatic. In preferred embodiments B is an unsubstituted or substituted phenyl, napthyl or pyridyl.

Exemplary preferred Q groups include the following:

Amidino groups such as B-Q wherein Q is;

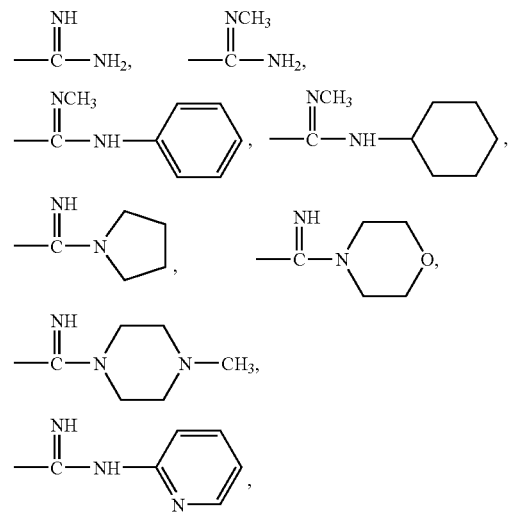

Iminoalkyleneamino groups such as B-Q wherein Q is;

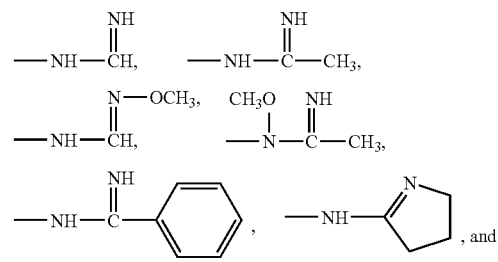

Guanidino groups such as B-Q;

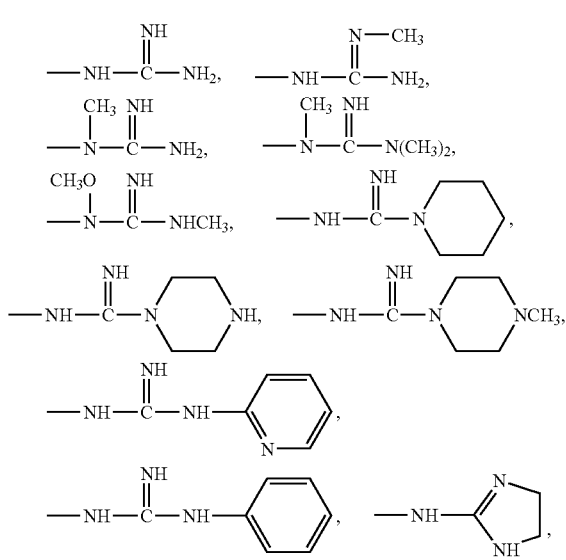

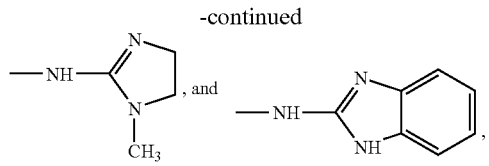

Preferred Q groups are the amidino groups and guanidino groups above and especially an B-amidino or B-guanidino wherein B is defined above. B is preferably a substituted or unsubstituted phenyl, napthyl, or pyridyl.

Listed below are various representative parent pharmaceutical agents which can be used and which contain an appropriate polar or basic function. One skilled in the art will realize that the list below is not exclusive and the invention is applicable to other equivalent drugs, pharmaceuticals, or medicaments.

Acetic acid, [[1-[2-[[4-(aminoiminomethyl)benzoyl] amino]-3-(4-hydroxyphenyl)-1-oxopropyl]-4-piperidinyl]oxy]-, (S)-

Acetic acid, [[1-[2-[[4-(aminoiminomethyl)benzoyl] amino]-3-(methyl)-1-oxopropyl]-4-piperidinyl]oxy]-, (S)-

Acetic acid, [[1-[2-[[4-(aminoiminomethyl)benzoyl] amino]-3-(methyl)-1-oxopropyl]-4-piperidinyl]oxy]-, ethyl ester (S)-

Acetamide, N-[1-[[4-(aminoiminomethyl)phenyl]methyl]-2-oxo-2-(1-piperidinyl)ethyl]-2-[(2-naphthalenylsulfonyl)amino]-, (S)-

Acetic acid, [[4-[[[6-(aminoiminomethyl)-2-quinolinyl]carbonyl]amino]cyclohexyl]oxy]-, trans-, L-Alanine, 3-[[[3-[4-(aminoiminomethyl)phenyl]-4,5-dihydro-5-isoxazolyl]acetyl]amino]-N-(butoxycarbonyl)-, (R)-

L-Alanine, 3-[[[3-[4-(aminoiminomethyl)phenyl]-4,5-dihydro-5-isoxazolyl]acetyl]amino]-N-(butoxycarbonyl)-, (R)-, methyl ester L-Alanine, 3-[[[3-[4-(aminoiminomethyl)phenyl]-4,5-dihydro-5-isoxazolyl]acetyl]amino]-N-[(3-methylphenyl)sulfonyl]-, methyl ester Alanine, 3-[[[3-[4-(aminoiminomethyl)phenyl]-4,5-dihydro-5-isoxazolyl]acetyl]amino]-N-(butoxycarbonyl)-, methyl ester, Benzamide, 4-(aminoiminomethyl)-N-[[1-[3-hydroxy-2-[(2-naphthalenylsulfonyl)amino]-1-oxopropyl]-2-pyrrolidinyl]methyl]-,[S-(R*,R*)]-, Benzamide, 3-(aminoiminomethyl)-N-[[1-[3-hydroxy-2-[(2-naphthalenylsulfonyl)amino]-1-oxopropyl]-2-pyrrolidinyl]methyl]-,[S-(R*,R*)]-

4H-1,4-Benzodiazepine-4-propanoic acid, 7-[[4-(aminoiminomethyl)phenyl]ethynyl]-1,2,3,5-tetrahydro-1-methyl-2,5-dioxo-, 4H-1,4-Benzodiazepine-4-propanoic acid, 7-[[4-(aminoiminomethyl)phenyl]ethynyl]-1-methyl-1,2,3,5-tetrahydro-2,5-dioxo-, ethyl ester, 4H-1,4-Benzodiazepine-4-propanoic acid, 7-[[4-(aminoiminomethyl)phenyl]ethynyl]-1,2,3,5-tetrahydro-.beta.,1-dimethyl-2,5-dioxo- 4H-1,4-Benzodiazepine-4-propanoic acid, 7-[[4-(aminoiminomethyl)phenyl]ethynyl]-1,2,3,5-tetrahydro-.alpha.,1-dimethyl-2,5-dioxo- 4H-1,4-Benzodiazepine-4-propanoic acid, 7-[[4-(aminoiminomethyl)phenyl]ethynyl]-1,2,3,5-tetrahydro-.beta.,1-dimethyl-2,5-dioxo-, ethyl ester 4H-1,4-Benzodiazepine-4-propanoic acid, 7-[[4-(aminoiminomethyl)phenyl]ethynyl]-1,2,3,5-tetrahydro-.alpha.,1-dimethyl-2,5-dioxo-, ethyl ester 4H-1,4-Benzodiazepine-4-propanoic acid, 7-[[4-(aminoiminomethyl)benzoyl]amino]-1,2,3,5-tetrahydro-1-methyl-2,5-dioxo-, 4H-1,4-Benzodiazepine-4-propanoic acid, 7-[[4-(aminoiminomethyl)benzoyl]amino]-1,2,3,5-tetrahydro-1-methyl-2,5-dioxo-, ethyl ester, 4H-1,4-Benzodiazepine-4-propanoic acid, 7-[[4-(aminoiminomethyl)benzoyl]amino]-1,2,3,5-tetrahydro-.beta.,1-dimethyl-2,5-dioxo- 4H-1,4-Benzodiazepine-4-propanoic acid, 7-[[4-(aminoiminomethyl)benzoyl]amino]-1,2,3,5-tetrahydro-.beta.,1-dimethyl-2,5-dioxo-, ethyl ester 4H-1,4-Benzodiazepine-4-propanoic acid, 7-[[4-(aminoiminomethyl)benzoyl]amino]-1,2,3,5-tetrahydro-.alpha.,1-dimethyl-2,5-dioxo- 4H-1,4-Benzodiazepine-4-propanoic acid, 7-[[4-(aminoiminomethyl)benzoyl]amino]-1,2,3,5-tetrahydro-.alpha.,1-dimethyl-2,5-dioxo-, ethyl ester 4H-1,4-Benzodiazepine-4-propanoic acid, 6-chloro-7-[[4-(aminoiminomethyl) benzoyl]amino]-1,2,3,5-tetrahydro-1-methyl-2,5-dioxo-, 4H-1,4-Benzodiazepine-4-propanoic acid, 6-chloro-7-[[4-(aminoiminomethyl) benzoyl]amino]-1,2,3,5-tetrahydro-1-methyl-2,5-dioxo-, ethyl ester, 4H-1,4-Benzodiazepine-4-propanoic acid, 6-chloro-7-[[4-(aminoiminomethyl) benzoyl]amino]-1,2,3,5-tetrahydro-1-methyl-2,5-dioxo-, isopropyl ester, 4H-1,4-Benzodiazepine-4-propanoic acid, 6-chloro-7-[[4-(aminoiminomethyl) benzoyl]amino]-1,2,3,5-tetrahydro-1-methyl-2,5-dioxo-, sec-butyl ester, 4H-1,4-Benzodiazepine-4-propanoic acid, 6-chloro-7-[[4-(aminoiminomethyl) benzoyl]amino]-1,2,3,5-tetrahydro-.beta.,1-dimethyl-2,5-dioxo- 4H-1,4-Benzodiazepine-4-propanoic acid, 6-chloro-7-[[4-(aminoiminomethyl) benzoyl]amino]-1,2,3,5-tetrahydro-.beta.,1-dimethyl-2,5-dioxo-, ethyl ester 4H-1,4-Benzodiazepine-4-propanoic acid, 6-chloro-7-[[4-(aminoiminomethyl) benzoyl]amino]-1,2,3,5-tetrahydro-alpha.,1-dimethyl-2,5-dioxo- 4H-1,4-Benzodiazepine-4-propanoic acid, 6-chloro-7-[[4-(aminoiminomethyl) benzoyl]amino]-1,2,3,5-tetrahydro-.alpha.,1-dimethyl-2,5-dioxo-, ethyl ester 4H-1,4-Benzodiazepine-4-propanoic acid, 6-chloro-7-[[4-(aminoiminomethyl) benzoyl]amino]-1,2,3,5-tetrahydro-.alpha.,1-dimethyl-2,5-dioxo-, isopropyl ester 4H-1,4-Benzodiazepine-4-propanoic acid, 6-chloro-7-[[4-(aminoiminomethyl) benzoyl]amino]-1,2,3,5-tetrahydro-.alpha.,1-dimethyl-2,5-dioxo-, sec-butyl ester 4H-1,4-Benzodiazepine-4-propanoic acid, 7-[[4-(aminoiminomethyl)phenyl]methoxy]-1,2,3,5-tetrahydro-1-methyl-2,5-dioxo- 4H-1,4-Benzodiazepine-4-propanoic acid, 7-[[4-(aminoiminomethyl)phenyl]methoxy]-1,2,3,5-tetrahydro-1-methyl-2,5-dioxo-, ethyl ester Benzoic acid, 4-[(aminoiminomethyl)amino]-, 6-(aminoiminomethyl)-2-naphthalenyl ester, Benzenepropanoic acid, 4-[1-[4-(aminoiminomethyl)phenyl]-2,5-dihydro-4-methoxy-2-oxo-1H-pyrrol-3-yl]-2-

Benzofuranpropanoic acid, 5-(aminoiminomethyl)-.alpha.-[4-(3-pyrrolidinyloxy)phenyl]-, ethyl ester, Benzenecarboximidamide, 4,4'-[1,5-pentanediylbis(oxy)] bis- Benzenecarboximidamide, 4-[2-amino-3-oxo-3-(1-piperidinyl)propyl]-, (R)-

Benzoic acid, 4-methoxy-, 4-(aminoiminomethyl)phenyl ester 1H-1,4-Benzodiazepine-2-acetic acid, 7-[[[4-(aminoiminomethyl)phenyl]amino]carbonyl]-2,3,4,5-tetrahydro-3-oxo-4-(2-phenylethyl)-

1H-2-Benzazepine-4-acetic acid, 7-[[[4-(aminoiminomethyl)phenyl]methyl amino]carbonyl]-2,3,4,5-tetrahydro-3-oxo-2-(2-phenylethyl)-

1H-2-Benzazepine-4-acetic acid, 7-[[[4-(aminoiminomethyl)phenyl]methyl amino]carbonyl]-2,3,4,5-tetrahydro-3-oxo-2-(2-phenylethyl)-, methyl ester 1H-2-Benzazepine-4-acetic acid, 7-[[4-(aminoiminomethyl)benzoyl]amino]-2,3,4,5-tetrahydro-3-oxo-2-(2-phenylethyl)-, methyl ester Benzenecarboximidamide, 4-[octahydro-3-methyl-4,6-dioxo-5-(phenylmethyl)pyrrolo[3,4-c]pyrrol-1-yl]-, (1.alpha.,3.beta.,3a.beta.,6a.beta.)-

5-Benzofurancarboximidamide, 2,2'-(1,2-ethanediyl)bis-

Carbamic acid, [[4(aminoiminomethyl)phenyl]phosphonomethyl]-, C-(phenylmethyl) ester, (R)-

Carbamic acid, [1-[[4-(aminoiminomethyl)phenyl]methyl]-2-oxo-2-(1-piperidinyl)ethyl]-, phenylmethyl ester Cyclohexanecarboxylic acid, 4-[[[[6-(aminoiminomethyl)-2-naphthalenyl]oxy]acetyl]amino]-, Cyclohexanecarboxylic acid, 4-[[[[6-(aminoiminomethyl)-2-naphthalenyl]oxy]acetyl]amino]-, methyl ester Butanoic acid, 4-[[1-[[4-(aminoiminomethyl)phenyl]methyl]-2-oxo-2-(1-piperidinyl)ethyl]amino]-3-[[(4-methoxy-2,3,6-trimethylphenyl)sulfonyl]amino]-4-oxo-, [S-(R*,S*)]-

Carbamicacid,[[4(aminoiminomethyl)phenyl](diphenoxyphosphinyl)methyl]-, phenylmethyl ester, (R)-

Glycinamide, N-acetyl-4-(aminoiminomethyl)-L-phenylalanyl-L-2-cyclohexyl-N-[(1-methylpyridinium-4-yl)methyl]-, iodide Glycinamide, N-acetyl-4-(aminoiminomethyl)-D-phenylalanyl-L-2-cyclohexyl-N-[(1-methylpyridinium-4-yl)methyl]-, iodide Glycinamide, N-acetyl-4-(aminoiminomethyl)-L-phenylalanyl-N-[[4-(aminoiminomethyl)phenyl]methyl]-L-2-cyclohexyl- Glycinamide, N-acetyl-4-(aminoiminomethyl)-L-phenylalanyl-L-2-cyclohexyl-N-[1-(1-methylpyridinium-4-yl)ethyl]-, iodide, Glycine, DL-2-[4-(aminoiminomethyl)phenyl]-N-(1-D-phenylalanyl-L-prolyl)-

Glycine, N-[N-2[[[4(aminoiminomethyl)phenyl]sulfonyl]amino]-4-methyl-1-oxopentyl]glycyl]-2-phenyl-, ethyl ester( 1H-Imidazo[4,5-b]pyridine-1-carboxylic acid, 5-[[4-(aminoiminomethyl)benzoyl]amino]-2,3-dihydro-2-oxo-3-(2-phenylethyl)-, methyl ester Morpholine, 4-[3-[4-(aminoiminomethyl)phenyl]-2-[3-[[(6,7-dimethoxy-2-naphthalenyl)sulfonyl]amino]-2-oxo-1-pyrrolidinyl]-1-oxopropyl]-

2-Naphthalenepropanoic acid, 7-(aminoiminomethyl)-.alpha.-[4-[[1-(1-iminoethyl)-3-pyrrolidinyl]oxy]phenyl]-, [S-(R*,R*)]-

2-Naphthalenepropanoic acid, 7-(aminoiminomethyl)-.alpha.-[4-[[1-(1-iminoethyl)-3-pyrrolidinyl]oxy]phenyl]-, [R-(S*,S*)]-

2-Naphthalenepropanoic acid, 7-(aminoiminomethyl)-.alpha.-[4-[[1-(1-iminoethyl)-3-pyrrolidinyl]oxy]phenyl]-, [R-(R*,R*)]-

-2-Naphthalenepropanoic acid, 7-(aminoiminomethyl)-.alpha.-[4-(3-pyrrolidinyloxy)phenyl]-, [S-(R*,R*)]-

2-Naphthalenepropanoic acid, 7-(aminoiminomethyl)-.alpha.-[4-[[1-(1-iminoethyl)-3-pyrrolidinyl]oxy]phenyl]-, ethyl ester, including the [S-,(R*,R*)]enantiomer, Pentanamide, 2-[[[4(aminoiminomethyl)phenyl]sulfonyl]amino]-N-[[(diphenylmethyl)amino]acetyl]-4-methyl-, (S)-

4-Pentynoic acid, 3-[[4-[[4-(aminoiminomethyl)phenyl]amino]-1,4-dioxobutyl]amino]-, ethyl ester Phenylalanine, 3-(aminoiminomethyl)-N-[N-[(4-methylphenyl)sulfonyl]glycyl]-, methyl ester, Phenylalaninamide, 1-[(phenylmethoxy)carbonyl]-L-prolyl-4-(aminoiminomethyl)-N-butyl-, 4-Piperidineacetic acid, 1-[[[6-(aminoiminomethyl)-2-naphthalenyl]oxy]acetyl]-

4-Piperidineacetic acid, 1-[[[6-(aminoiminomethyl)-2-naphthalenyl]oxy]acetyl]-, methyl ester Piperidine, 1-[4-(aminoiminomethyl)phenyl]-N-[N-[(4-methoxy-2,3,6-trimethylphenyl)sulfonyl]-O-(2,3,4-tri-O-acetyl-.beta.-D-ribopyranosyl)-L-seryl]-D-phenylalanyl]-

Piperidine, 1-[3-[4-(aminoiminomethyl)phenyl]-2-[3-[(2-naphthalenylsulfonyl)amino]-2-oxo-1-pyrrolidinyl]-1-oxopropyl]-, [S-(R*,R*)]-

Piperidine, 1-[3-[3-(aminoiminomethyl)phenyl]-2-[(2-naphthalenylsulfonyl)amino]-1-oxopropyl]-4-methyl-, (S)-

Piperidine, 1-[3-[3-(aminoiminomethyl)phenyl]-2-[(2-naphthalenylsulfonyl)amino]-1-oxopropyl]-4-methyl-, (R)-

1-Piperidinineacetic acid, 4-[4-[4-(aminoiminomethyl)phenyl]-1-piperazinyl]-

4-Piperidineacetic acid, 1-[[4'-(aminoiminomethyl)[1,1'-biphenyl]-4-yl]carbonyl]-, cyclohexyl ester, 4-Piperidineacetic acid, 1-[[4'-(aminoiminomethyl)[1,1'-biphenyl]-4-yl]carbonyl]-, cyclopentyl ester 1-piperazineethanol, 4-[3-[3-(aminoiminomethyl)phenyl]-2-[(2-naphthalenylsulfonyl)amino]-1-oxopropyl]-, (S)-

L-Phenylalanine, N-[N-[5-[4-(aminoiminomethyl)phenyl]-1-oxopentyl]-L-.alpha.-aspartyl]-

L-Phenylalanine, N-[N-[3-[[4-(aminoiminomethyl)phenoxy]methyl]benzoyl]-L-.alpha.-aspartyl]-, bis(1,1-dimethylethyl) ester L-Prolinamide, N-methyl-D-phenylalanyl-N-[[4-(aminoiminomethyl)phenyl]methyl]-

L-Prolinamide, D-phenylalanyl-N-[[4-(aminoiminomethyl)phenyl]methyl]-

L-Prolinamide, D-phenylalanyl-N-[[4-(aminoiminomethyl)phenyl]methyl]-N-methyl-

L-Prolinamide, D-phenylalanyl-N-[2-[4-(aminoiminomethyl)phenyl]ethyl]-

L-Prolinamide, D-phenylalanyl-N-[[4-(aminoiminomethyl)phenyl]methyl]-N-methyl-

L-Prolinamide, N-[(1,1-dimethylethoxy)carbonyl]-D-phenylalanyl-N-[[4-(aminoiminomethyl)phenyl]methyl]-3-(aminoiminomethyl)phenylalanine L-Prolinamide, N-methyl-N-[(phenylmethoxy)carbonyl]-D-phenylalanyl-N-[[4-(aminoiminomethyl)phenyl]methyl]-

L-Prolinamide, N-acetyl-4-(aminoiminomethyl)-L-phenylalanyl-L-isoleucyl-L-arginyl-L-leucyl- L-Prolinamide, N-acetyl-L-tyrosyl-L-2-cyclohexylglycyl-4-(aminoiminomethyl)-L-phenylalanyl-L-leucyl- L-Prolinamide, 2-[[4-(aminoiminomethyl)phenyl]methyl]-N,N-bis(1-methylethyl)-3-oxo-.beta.-alanyl-L-2-cyclohexylglycyl-L-arginyl-L-leucyl- L-Prolinamide, N-(carboxymethyl)-D-2-cyclohexylglycyl-N-[[4-(aminoiminomethyl)phenyl]methyl]-

L-Prolinamide, 3-cyclohexyl-D-alanyl-N-[[4-(aminoiminomethyl) phenyl]methyl]-

L-Prolinamide, N-(carboxymethyl)-3-cyclohexyl-D-alanyl-N-[[4-(aminoiminomethyl)phenyl]methyl]-

2-Pyridinecarboxylic acid, 1-[3-[3-(aminoiminomethyl)phenyl]-1-oxo-2-[[(1,2,3,4-tetrahydro-2-methyl-7-isoquinolinyl)sulfonyl]amino]propyl]-1,2,3,6-tetrahydro-4-methyl-,
2-Pyridinecarboxylic acid, 1-[3-[3-(aminoiminomethyl)phenyl]-1-oxo-2-[[(1,2,3,4-tetrahydro-2-methyl-6-isoquinolinyl)sulfonyl]amino]propyl]-1,2,3,6-tetrahydro-4-methyl-, ethyl ester, [S-(R*,S*)]-
2-Pyridinecarboxylic acid, 1-[3-[3-(aminoiminomethyl)phenyl]-1-oxo-2-[[(1,2,3,4-tetrahydro-2,5-dimethyl-8-isoquinolinyl)sulfonyl]amino]propyl]-1,2,3,6-tetrahydro-4-methyl-, ethyl ester, [S-(R*,S*)]-
Octanoic acid, 8-[4-(aminoiminomethyl)phenoxy]-, ethyl ester,
[S-(R*,R*)]-7-(aminoiminomethyl)-a-[4-[[1-(1-iminoethyl)-3-pyrrolidinyl]oxy]phenyl-2-naphthalenepropanoic acid
3-Oxazolidineacetic acid, 4-[[4-[[4-(aminoiminomethyl)phenyl]methoxy]phenyl]methyl]-2-oxo-, ethyl ester, (S)-
3-Oxazolidineacetic acid, 4-[[4-[[4-(aminoiminomethyl)phenyl]methoxy]phenyl]methyl]-2-oxo-, (S)-
L-Tyrosinamide, N-[[4-(aminoiminomethyl)phenoxy]acetyl]glycyl-L-alpha.-aspartyl-O-methyl-,
L-Valine, N-[N-[4-[4-(aminoiminomethyl)phenoxy]-1-oxobutyl]-L-.alpha.-aspartyl]-
3-Pyrrolidineacetic acid, 5-[[[4'-[imino[(amino]methyl][1,1'-biphenyl]-4-yl]oxy]methyl]-2-oxo-methyl ester,
1-Piperidineacetic acid, 4-[4-[4-(aminoiminomethyl)phenyl]-1-piperazinyl]-,
1,3-piperazinediacetic acid, 4-[[[4-(aminoiminomethyl)benzoyl]amino]acetyl]-2-oxo-, 3-methyl ester.

Preferred are drugs or pharmaceuticals containing an amidino functionality used for the treatment of cardiovascular disease. More preferred still are drugs or pharmaceuticals containing amidine functionality used as antithrombotics. Most preferred are drugs or pharmaceuticals containing amidine functionality that are glycoprotein IIb/IIIa antagonists, Factor Xa, Factor VIIa, trypsin or thrombin inhibitors.

In preferred embodiments the present invention relates to prodrugs of guanidine, thioguanidine or amidine containing compounds which are pharmaceutically active and, for example, are useful in inhibiting formation of thrombin, or in inhibiting platelet aggregation, or as fibrinogen receptor antagonists, and the like, such as those described in, for example:
U.S. Pat. No. 5,599,793;
International Publication Number 95/04057;
Bondinell et al., (1994) Bioorganic & Medicinal Chem., 2(9):897–908;
Cook et al., (1993) Thrombosis and Haemostasis, 70(3): 531–539;
Frederick et al., (1996) Circulation 93(1):129–134;
Cox et al., (1996) Thrombosis and Haemostasis 75(3): 503–509;
Aoki et al., (1996) Throm. Res. 81(4):439–450;
Carteuax et al., Throm. and Haem. 70(5):817–821;
International Publication Number WO 95/14682;
Hodohara et al., (1995) Pathophysiol. 2:145–151;
Sall et al., (1996) Bioorganic and Medicinal Chem. Letts. 6(1):81–86;
Xue et al., (1996) Bioorganic and Medicinal Chem. Letts. 6(3):339–344;
Colin et al., (1994) J. Med. Chem. 37:3882–3885;
Bovy et al., (1994) Bioorg. and Med. Chem. 2(9):881–895];
Stürzebecher et al., (1989) Thromb. Res. 54:245–252;
Hara et al., (1994) Thromb. and Haem. 71(3)314–319],
Bertrand et al., (1996) 35:3147–3155;
International Publication Number WO 93/08174;
International Publication Number WO 95/04057 and U.S. Pat. No. 5,565,449;
International Publication Number WO 95/35312;
International Publication Number WO 96/24609;
International Publication Number WO 95/13274;
Dickneite et al., (1995) Thromb. Res. 77(4):357–368;
Mack et al., (1995) J. Enzyme Inhibition 9:73–86;
Pierschbacher and Ruoslahti, (1987) J. Biol. Chem. 262: 17294; and
European Patent Application No. 89910207).

Prefered prodrugs of the present invention include 2,2,2-trichloroethoxycarbonyl derivatives of the GPIIb/IIIa antagonists described in International Publication No. WO 93/08174 and U.S. Pat. No. 5,565,449 the disclosures of which are specifically incorporated herein by reference.

Preferred among these compounds are compounds of the general structure (I)

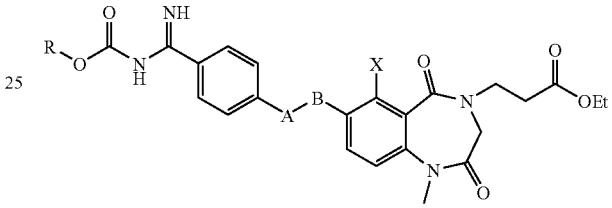

wherein A–B is:

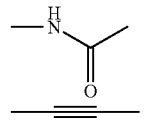

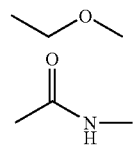 and

X is H and R is —CH₂CCl₃.

Whereas improvement in oral bioavailability is seen in compounds where the polar or basic N containing moiety is converted into the trichloroalkoxycarbonyl derivative as described herein, generally greater improvement in oral bioavailability is seen in compounds where both a carboxylate and an N-containing group such as an amidine group are derivatized. Therefore, the compounds of this invention are meant to include those compounds wherein both a carboxylate and at least one appropriate Q group as described herein have been derivatized.

By way of example and not limitation, carboxyl groups are commonly derivatized by a hydroxyl group, an optionally substituted alkoxy, for example a lower (C1–6)alkylamino or a N,N-dilower (C1–4)alklyamino, or an optionally substituted alkoxy, for a example a lower (C1–6)alkoxy whose alkyl moiety is optional substituted by hydroxy or an optionally substituted amino, for example amino, dimethyl amino, diethylamine, diethylamino, piperidino or morpholino) halogen, a lower (C1–6)alkoxy, a lower(C1–6) alkythio or an optionally substituted dioxolenyl (for example 5-methyl 2 oxo 1,3-dioxolenyl or a group represented by the formula of —OCHROCOR (EP 0529 858 A1)).

The compounds of this invention can be produced by, for example, the methods described herein below. In the following description where the parent compound contains functional groups such as carboxyl groups and other amino groups, these functional groups may, when necessary, be protected with a protective group conventionally used in the field of organic synthesis. Introduction and elimination of protecting groups may be conducted in accordance with conventional practice. The formation reaction may require the protection of the carboxy groups using one of, for example, the exter derivatives of the carboxylic acid group commonly employed to block or protect the carboxylic acid group while reactions are carried out on other functional groups. Carboxy-protecting groups are known in the art. The formation reactions may also require the protection of, for example, primary and secondary amines which may be affected by the use of a protective group such as tert-butoxycarbonyl, benxyloxycarbonyl, p-nitrobenzyloxy carbonyl and triphenylmethyl or the like.

The compounds of the present invention can be prepared by conventional methods. An exemplary method for producing the prodrugs of the instant invention can be depicted as follows:

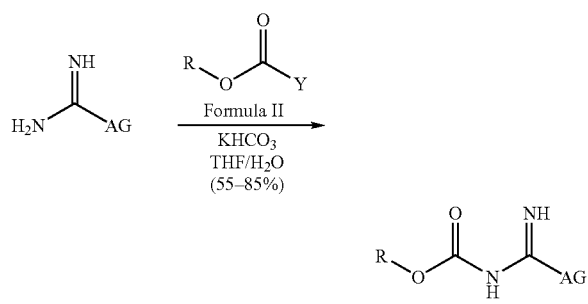

The first step of the method for preparing the prodrugs of the present invention consists of reacting a parent drug or pharmaceutical agent as described above with an alkyl formate compound of formula II where Y represents a halogen such as chlorine or an amino conjugate such as a pyrimidinium ion or a good leaving group such as a substituted phenoxy as, for example p-nitrophenoxy, dinitrophenoxy, flourophenoxy or diflourophenoxy. The reaction is carried out in solvents such as dichloromethane, dichloroethane, tetrahydrofuran, dioxane, diethyl ether, dimethoxyethane and the like or other solvents such as ethylacetate or acetonitrile. The reaction can be carried out at temperatures from −78 C to 50 C but preferably carried out at 1 C to room temperature. In the above exemplary schmatic R refers to the halo-alkyl group. The reaction is carried out in the presence of a base such as potassium bicarbonate, pyridine, triethylamine, 1,8-bis(dimethyl amino), napthalene, N-methylmorpholine and the like.

Compounds so obtained can be isolated from the reaction mixture by conventional separation and purification means such as extraction, concentration, neutralization, recrystalization, column chromatography and thin-layer chromatography.

The prodrugs of the instant invention can be used in a manner analogous to the parent compound. Therefore, when the AG-Q group is a thrombin inhibitor, the prodrug will be useful as a thrombin inhibitor in dosages and dosage forms as described for the particular thrombin inhibitor. If the AG-Q group is an inhibitor of platelet aggregation, the prodrug will be useful as an inhibitor of platelet aggregation in dosages and dosage forms as described for the inhibitor of platelet aggregation. It is understood that the specific dose of a compound administered according to this invention to obtain a therapeutic or prophylactic effect will, of course, be determined by the particular parent pharmaceutical agent and further by the particular circumstances surrounding the administration, including, for example, the condition being treated. Typical daily doses of the compounds are between about 0.01 mg/kg and about 100 mg/kg. The dose regime will understandably vary. For example, several above noted parent agents may be administered prophylactically as a single daily dose or in multiple doses such as between 2 and 5 times per day as appropriate.

Depending upon the AG-Q group employed the compounds of the present invention may be serine protease inhibitors and in particular may inhibit thrombin, Factor Xa, Factor VIIa and/or trypsin. Such compounds are useful for the treatment and prevention of those particular processes which involve the production and/or action of thrombin. This includes thrombotic and prothrombotic conditions in which the coagulation cascade is activated and condition wherein a large number of cells (such as neutrophls, fibroblasts, endothelial cells, smooth muscle cells) are activated. Therefore the uses include but are not limited to the treatment and prevention of peripheral arterial obstruction, acute myocardial infarction, deep vein thrombosis, pulmonary embolism, dissecting aneurysm, transient ischemic attack, restenosis, stroke and other occlusive disease or disorders such as unstable angina, disseminated intravascular coagulation, sepsis, surgical or infective shock, postoperative and post-delivery trauma, angioplasty, cardiopulmonary bypass and coronary bypass, incompatible blood transfusion, amotio placentae, thrombotic thrombocytopenic purpura, asthma, chronic or acute renal disease, diabetes, inflammations, atherosclerosis, hemolytic uremic syndrome, symmetric peripheral necrosis, and allograft rejection in mammals including human.

Such AG-Q compounds and hence the prodrugs of the instant invention can be used for enhancing the action of a thrombolytic agent and for preventing reobstruction after percutaneous transluminal coronary recanalization, preventing reobstruction after percutaneous transluminal coronary angioplasty and preventing thrombocytopenia due to dialysis, for example.

As a further example, the glycoprotein IIb/IIIa appears on the surface of platelets as a noncovalent heterodimeric complex and has been shown to interact with, fibronectin, vitronectin, von Willebrand factor, and thrombospondin. These adhesive proteins contain Arg-Gly-Asp (RGD) sequences which serve as a basic recognition feature for binding GPIIb/IIIa and certain other integrins. In various binding studies, small peptides containing the RGD fragment have been shown to successfully compete with larger proteins (see references, supra). The interaction between the particular receptor and GPIIbIIIa is the common ultimate event in the aggregation cascade regardless of the mechanism of platelet activation. Arg-Gly-Asp-based antagonists of the platelet GPIIbIIIa/receptor interaction act as a stimulus-independent inhibitor of platelet aggregation (International Publication No. WO 95/04057). Therefore the compounds and hence the prodrugs of the instant invention can be used to prevent the development of blood platelet thrombosis and can be used in the treatment and prevention of diseases and disorders involving inappropriate or non-beneficial platelet aggregation or thrombosis.

The prodrugs of the instant invention can be administered topically, orally or parenterally such as subcutaneously, intravenously, as well as by nasal, rectal or sublingual application to various mammalian species including human. In preferred embodiments the pharmaceutical composition containing the prodrug of the instant invention may be in a unit form suitable for oral use, for example, as tablets, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such composition may contain one or more agents, such as those selected from the group consisting of sweetening agents, flavoring agents, coloring agents and preserving agents, in order to provide pharmaceutically palatable preparations.

Formulations for oral use include tablets which contain the prodrug in admixture with a non-toxic pharmaceutically acceptable excipients. These excipients may be, for example, inert diluents, such as calcium carbonate, sodium chloride lactose, calcium phosphate or sodium phosphate; granulating and disintegrating agents for example maize starch, gelatin or acacia and lubricating agents for example magnesium stearate, stearic acid or talc. The tablets may be coated by known techniques to delay disintegration and absorption in the gastrointestinal tract and thereby provide a sustained action over a longer period. For example a time delay material such as glycerol monostearate or glyceryl distearate may be employed. Formulation for oral use may also be presented as hard gelatin capsules wherein the prodrug is mixed with an inert solid diluent, for example calcium carbonate, calcium phosphate or kaolin, or as soft gelatin capsules wherein the active ingredient is mixed with water or an oil medium for example peanut oil, liquid paraffin or olive oil.

Aqueous suspensions usually contain the prodrug in admixture with appropriate excipients. Such excipients are suspending agents, for example sodium carboxymethycellulose, methylcellulose, hydroxypropylmethylcellulose, sodium alginate, polyvinylpyrrolidone, gum tragacanth and gum acacia, dispersing or wetting agents which may be a naturally-occurring phosphatide, for example, lecithin; a condensation product of an alkylene oxide with a fatty acid, for example, polyoxyethylene stearate, a condensation product of ethylene oxide with a long chain aliphatic alcohol for example heptadecaethyleneoxycetanol; a condensation product of ethylene oxide with a partial ester derived from fatty acids and a hexitol such as polyoxyethlene sorbitol monooleate or a condensation product of ethylene oxide with a partial ester derived from fatty acids and hexitol anhydrides, for example, polyoxyethylene sorbitol monooleate. The aqueous suspension may also contain one or more preservatives, for example, ethyl, n-propyl, or a p-hydroxybenzoate; one or more coloring agents; one or more flavoring agents; and one or more sweetening agents such as sucrose or saccharin.

Oily suspensions may be formulated by suspending the prodrug in a vegetable oil, for example, arachis oil, olive oil, sesame oil, peanut oil or coconut oil, or in mineral oil such as liquid paraffin. The oily suspensions may contain a thickening agent, for example beeswax, hard paraffin or cetyl alcohol. Sweetening agents such as those set forth above and flavoring agents may be added to provide a palatable oral preparation. These compositions may be preserved by the addition of an antioxidant such as ascorbic acid.

Dispersible powders and granules suitable for preparation of an aqueous suspension by the addition of water provide the active ingredient in admixture with a dispersing or wetting agent suspending agent and one or more preservatives. Suitable dispersing or wetting agents and suspending agents are exemplified above. Additional excipients may also be present.

The prodrugs may also be administered in the form of suppositories. These compositions can be prepared by mixing the prodrug with a suitable non-irritating excipient which is solid at ordinary temperatures but liquid at the rectal temperature and will therefore melt in the rectum to release the drug, for example cocoa butter and polyethylene glycols.

The following examples are offered by way of illustration and not by way of limitation. The disclosures of all citations in the specification are expressly incorporated herein by reference.

EXAMPLES

Example 1

Introduction

A GPIIb/IIIa binding epitope on fibrinogen consisting of the sequence Arg-Gly-Asp (RGD) has been identified and a number of synthetic peptides containing this sequence have been shown to be GPIIb/IIIa antagonists (see, Detailed Description of the Preferred Embodiments). Based upon the structural features of this RGD epitope, potent nonpeptidal antagonists of the general structure I have been prepared.

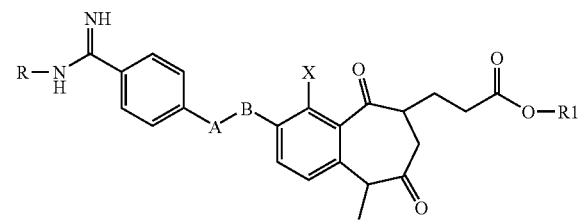

Structure I where, for example:

G6191 A-B=Y X=H R=Me, R1=R2=H $IC_{50}(PA)=59$ nM
G6249 A-B=W X=H R=Me, R1=R2=H $IC_{50}(PA)=120$ nM
G6703 A-B=X X=H R=Et, R1=R2=H $IC_{50}(PA)=76$ nM
G7464 A-B=Y X=Cl R=Me, R1=R2=H $IC_{50}(PA)=85$ nM

Where V, W, X and Y are

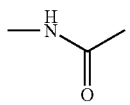

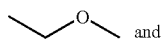 and

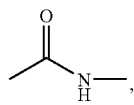, respectively and X is H for VWX and X is Cl for Y.

$IC_{50}$ are measured as ADP induced aggregation in citrated plasma.

Example 2

The preparation of mono and double prodrugs of these materials which masked the ionic charges were prepared and tested for oral bioavailability.

Methods

Mouse $ID_{50}$ were calculated from mice dosed at 100 mg/kg orally and sacrificed at either 1 or 3 hours timepoints, exsanguinated and ex vivo platelet aggregation measured to determine $ID_{50}$.

Compounds which had a mouse $ID_{50}$ less than 2 mg/kg were dosed in rats (50 mg/kg) to determine their oral bioavailability (% F).

Results

| | | | | Mouse $ID_{50}$ (mg/kg) | | | | | |
|---|---|---|---|---|---|---|---|---|---|
| R2 | R1 | G6191 | X | A-B | G6249 | X | A-B | G6703* | G7464** |
| H | H | 9.5 | H | CONH | 20 | H | -≡- | 20.3 | 7.2 |
| H | Et | 4.6 | H | CONH | 17 | H | -≡- | 1.8 | 11.7 |
| EtOCO | Et | 8.6 | H | CONH | 1.4 | H | -≡- | 0.9 | 0.5 |
| HO | Et | 6.8 | H | CONH | 2.7 | H | -≡- | 0.8 | 0.8 |
| HO | H | — | | | — | | | 22 | — |
| EtOCO | H | >25 | H | CONH | — | | | >25 | — |

*X = H, A-B = $CH_2O$
**X = Cl, A-B = CONH

| | | | Rat Oral Bioavailability (F) | | | |
|---|---|---|---|---|---|---|
| R2 | R1 | Parent= | G6191 | G6249 | G6703 | G7464 |
| H | H | | <0.5% | — | — | — |
| H | Et | | — | — | 2% | 2% |
| EtOCO | Et | | 1% | 5% | 6% | 6% |
| HO | Et | | — | — | 14% | 7% |

Because of this slow conversion less than 5% of the active drug was produced under these conditions. This result was confirmed in vivo by injecting rats with the double prodrug and measuring the amount of active metabolite produced. Again it was observed that little of the ethoxycarbonyl moiety was hydrolyzed to the amidine consistent with in vitro plasma stability results.

Example 3

Introduction

The compounds of Examples 4 through 9 were prepared according to the following procedure Methods General Procedure for Preparing N-2,2,2-Trichloroethoxycarbonyl Amidines. The amidino ester (1 mmole) and potassium bicarbonate (5 mmole) are dissolved in a mixture of tetrahydrofuran (6 ml) and water (2 ml). 2,2,2-trichloroethyl chloroformate (1.2 mmole) is added dropwise with vigorous stirring. The reaction is allowed to stir for one hour, poured into a separatory funnel and extracted three times with ethyl acetate (50 ml). The combined organic layer is washed once with saturated sodium bicarbonate solution, dried over anhydrous sodium sulfate, filtered and the ethyl acetate removed in vacuo. The crude product is purified using flash chromatography (ethyl acetate) to yield the final product as a white solid.

Example 4

4H-1,4-Benzodiazepine-4-propanoic acid, 7-[[4-(N-2,2,2-trichloroethoxycarbonylaminoiminomethyl)phenyl]methoxy]-1,2,3,5-tetrahydro-1-methyl-2,5-dioxo-, ethyl ester;

Yield 74%, m.p.: 82° C., $^1$HNMR ($CDCl_3$): 9.5 2(1H, bs, NH), 7.93 (2H, d, J=8.3, ArH), 7.5 (2H, d, J=8.3 Hz, ArH), 7.37 (1H, d, J=2.9 Hz, ArH), 7.20 (1H, d, J=8.8 Hz, ArH), 7.12 (1H, dd, J=8.8, J=3 Hz, ArH), 5.08 (2H, s, CCl3), 4.83 (2H, s, $PhCH_2O$), 4.18, (2H, q, J=7.3 Hz, $CH_3C\underline{H}_2O$), 3.6–4.05 (6H, complex multiplet, $CH_2N$), 2.72 (2H, dd, J=6.8 Hz, J=5.9 Hz, CH2CO), 1.25 (3H, t, J=6.8 Hz, $CH_3$), 1.17 (3H, t, J=7.3 Hz, $CH_3$).; $^{13}$CNMR ($CDCl_3$): 171.20, 168.80, 167.83, 166.70, 162.99, 155.76, 144.10, 133.83, 133.43, 130.74, 127.84, 127.34, 123.25, 120.05, 114.61, 75.25, 69.47, 60.76, 60.37, 52.52, 45.08, 42.70, 32.67, 14.08, 13.29.; MS (FAB+): 627 (100, M+H), 628, (35), 629 (100), 629 (30), 631 (33).

Exact Mass: Calculated for $C_{27}H_{30}N4O_7Cl_3$: 627.1180; Found: 627.1191

Example 5

4H-1,4-Benzodiazepine-4-propanoic acid, 6-chloro-7-[[4-(N-2,2,2-trichloroethoxycarbonylaminoiminomethyl)benzoyl]amino]-1,2,3,5-tetrahydro-.beta.,1-dimethyl-2,5-dioxo-, ethyl ester;

Yield=79%; $^1$H-NMR (CDCl$_3$): 9.50 (1H, bs, OCONH), 8.62 (1H, d, J=9.3 Hz, ArH), 8.60 (1H, s, CONH), 8.05 (2H, d, J=8.3 Hz, ArH), 7.94 (2H, d, J=8.3H, ArH), 7.22 (1H, d, J=9.3 Hz), 4.87 (2H, s, Cl$_3$CCH$_2$O), 4.14 (2H, q, J=7.0 Hz, CO$_2$CH$_2$), 4.08 (1H, d, J=15.1 Hz, COCH$_2$N), 4.03 (1H, dd, J=7.8, J=13.9 Hz, NCH$_2$CH$_2$CO), 3.86 (1H, d, J=15.1 Hz, COCH$_2$N), 3.85 (1H, m, NCH$_2$CH$_2$CO), 3.38 (3H, s, NCH$_3$), 2.73 (2H, m, CH$_2$CO$_2$Et), 1.27 (3H, t, J=7.1 Hz, OCH$_2$CH$_3$).; MS (FAB+): 660 (70, M+H), 661 (30), 662 (100), 663 (30), 664 (50);

Exact Mass: Calculated for C$_{26}$H$_{26}$Cl$_4$N$_5$O$_7$: 660.0507; Found: 660.0597;

Combustion Analysis: Calculated for C$_{26}$H$_{25}$Cl$_4$N$_5$O$_7$: C, 47.22, H, 3.81, N 10.59; Found:C, 47.56, H, 4.11, N, 10.27

Example 6

4H-1,4-Benzodiazepine-4-propanoic acid, 7-[[4-(N-2,2,2-trichloroethoxycarbonylaminoiminomethyl)phenyl]ethynyl]-1-methyl-1,2,3,5-tetrahydro-2,5-dioxo-, ethyl ester, Yield=58%; m.p.: 102° C.; $^1$H-NMR (CDCl$_3$): 9.50 (1H, bs, OCONH), 8.03 (1H, d, J=2.0 Hz, ArH), 7.93 (2H, d, J=8.5 Hz, ArH), 7.65 (1H, dd, J=2.0 Hz, 8.3 Hz, ArH), 7.60 (2H, d, J=8.4, ArH), 7.19 (1H, d, J=8.5 Hz, ArH), 4.87 (2H, s, Cl$_3$CCH$_2$O), 4.16 (2H, q, J=7.1 Hz, CO$_2$CH$_2$), 4.05 (1H, d, J=15.4 Hz, COCH$_2$N), 3.94 (3H, m, COCH$_2$N, NCH$_2$CH$_2$), 3.40 (3H, S, NCH3), 2.72 (2H, m, CH$_2$CO$_2$Et), 1.27 (3H, t, J=7.1 Hz, CO$_2$CH$_2$CH$_3$); $^{13}$C-NMR (CDCl$_3$): 171.8, 168.8, 166.3, 163.0, 141.0, 134.89, 134.23, 133.9, 131.78, 128.9, 127.58, 127.5, 121.11, 120.5, 95.5, 90.5, 75.24, 60.88, 52.0, 45.0, 35, 32.74, 14.13.; MS (FAB+): 607 (100 M+H), 608 (50), 609 (100), 610 (40), 611 (40)

Exact Mass: Calculated for C$_{27}$H$_{26}$Cl$_3$N$_4$O$_6$: 607.0839; Found: 607.0885;

Combustion Analysis: Calculated for C$_{27}$H$_{25}$Cl$_3$N$_4$O$_6$:C, 53.35, H, 4.15, N, 9.22 Found: C, 52.71, H, 4.24, N, 8.99.

Example 7

4H-1,4-Benzodiazepine-4-propanoic acid, 6-chloro-7-[[4-(N-2,2,2-trichloroethoxycarbonylaminoiminomethyl)benzoyl]amino]-1,2,3,5-tetrahydro-1-methyl-2,5-dioxo-, sec-butyl ester, Yield: 50% $^1$H-NMR (CDCl$_3$): 9.50 (1H, bs, OCONH), 8.65 (1H, d, J=9.3 Hz, ArH), 8.57 (1H, s, CONH), 8.03 (2H, d, J=8.3 Hz, ArH), 7.98 (2H, d, J=8.3H, ArH), 7.19 (1H, d, J=9.3 Hz), 4.85 (2H, s, Cl$_3$CCH$_2$O), 4.08 (3H, m,), 3.86 (4H, m,), 3.36 (3H, s, NCH$_3$), 2.75 (2H, m, CH$_2$CO$_2$Et), 1.52 (2H, m), 1.19 (3H, m, CH$_3$), 0.87 (3H, m, CH$_3$).; MS (FAB+): 688 (33, M+H), 689 (17), 690 (40), 691 (17), 692 (20),

Example 8

4H-1,4-Benzodiazepine-4-propanoic acid, 6-chloro-7-[[4-(N-2,2,2-trichloroethoxycarbonylaminoiminomethyl)benzoyl]amino]-1,2,3,5-tetrahydro-.alpha.,1-dimethyl-2,5-dioxo-, ethyl ester:

Yield: 70%; $^1$H-NMR (CDCl$_3$): 9.50 (1H, bs, OCONH), 8.62 (1H, m, ArH), 8.60 (1H, s, CONH), 8.05 (2H, m, ArH), 7.94 (2H, m, ArH), 7.22 (1H, t, J=9.3 Hz), 7.00 (1H, bs); 4.87 (2H, s, Cl$_3$CCH$_2$O), 4.1–4.3 (4H, m; CO$_2$CH$_2$, COCH$_2$N, NCH$_2$CH$_2$CO), 3.4–4.0 (2H, m, COCH$_2$N), 3.38 (3H, s, NCH$_3$), 2.93 (1H, m, CHCO$_2$Et), 1.27 (6H, m, 2×CH$_3$). MS (FAB+): 674 (m+H), 675, 676,

Example 9

4H-1,4-Benzodiazepine-4-propanoic acid, 6-chloro-7-[[4-(aminoiminomethyl) benzoyl]amino]-1,2,3,5-tetrahydro-1-methyl-2,5-dioxo-, isopropyl ester, Yield: 45%; $^1$H-NMR (CDCl$_3$): 9.50 (1H, bs, OCONH), 8.67 (1H, d, J=8.9 Hz, ArH), 8.61 (1H, s, CONH), 8.10 (2H, d, J=9.5 Hz, ArH), 8.01 (2H, d, J=9.5H, ArH), 7.22 (1H, d, J=. 8.9 Hz), 5.02 (1H, m, OCH(CH$_3$)$_2$), 4.88 (2H, s, Cl$_3$CCH$_2$O), 4.10 (1H, d, J=14.1 Hz, COCH$_2$N), 4.02 (1H, dd, J=7.8, J=13.9 Hz, NCH$_2$CH$_2$CO), 3.86 (1H, d, J=14.1 Hz, COCH$_2$N), 3.85 (1H, m, NCH$_2$CH$_2$CO), 3.39 (3H, s, NCH$_3$), 2.73 (2H, m, CH$_2$CO$_2$Et), 1.24 (6H, q, J=6.3 Hz, OCH(CH$_3$)$_2$).; MS (FAB+): 674 (m+H), 675, 676,

Example 10

In Vitro Plasma Stability

Introduction

In order to test whether the above modified alkoxycarbonyl amidines possessed increased physiological lability, a number of compounds were submitted to in vitro plasma stability studies.

Methods

Compounds were incubated in rat plasma at 37 C for 30 minutes. The samples were then analyzed by HPLC to determine the amount of parent produced.

Results

Figure 1:
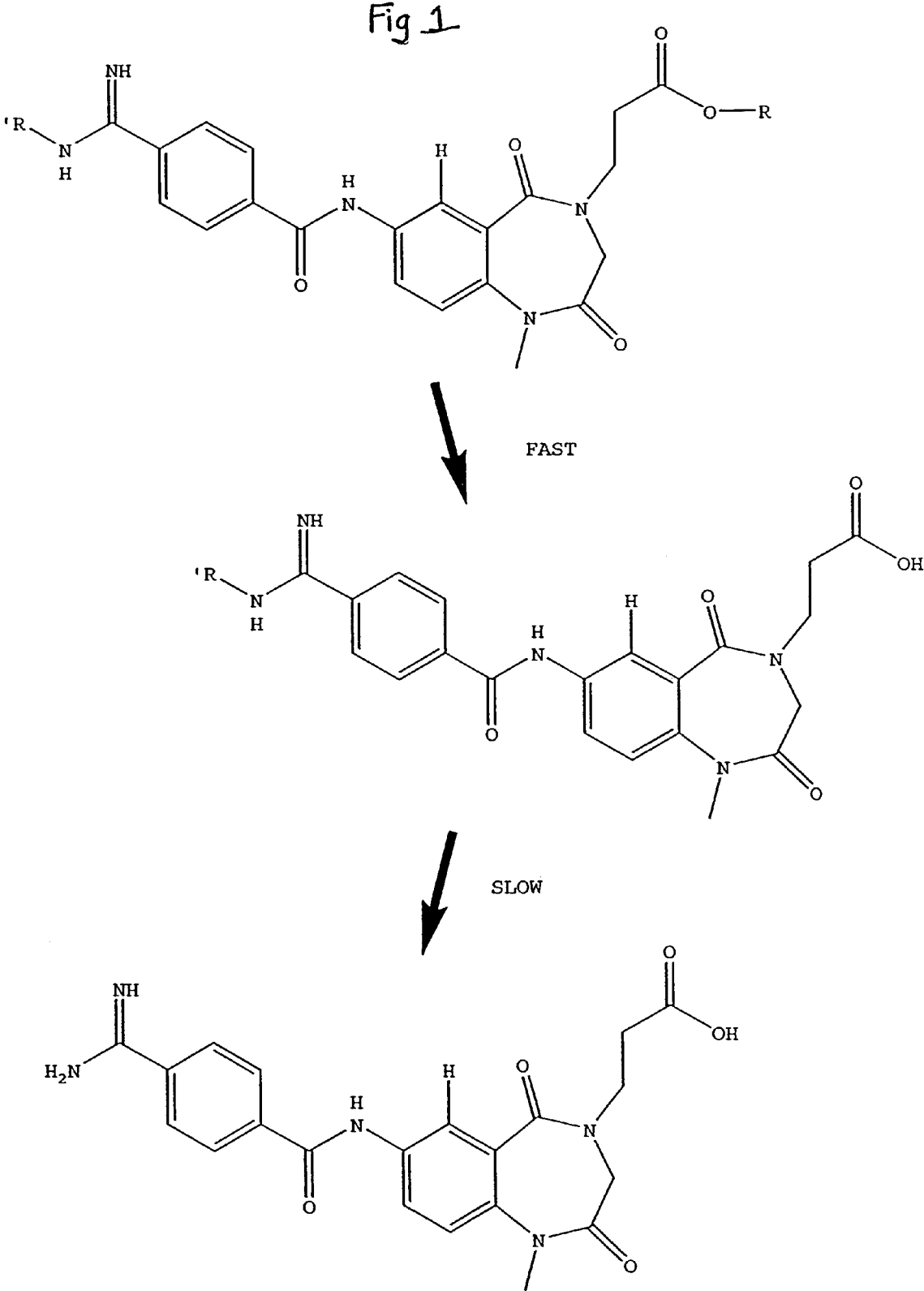
FIG. 1: A variety of alkoxycarbonylamidines were prepared including benzyloxy-butoxy, isobutoxy, (4-pyridyl) methoxy-, 1-morpholinoethoxy-, however no increases in oral bioavailability relative to the ethoxycarbonyl compounds were observed in any parent class. As part of a program to understand why these alkoxy carbonyl prodrugs were showing low oral availability, in vitro and in vivo studies were conducted to identify whether prodrug to parent conversion was limiting the oral activity. As schematically depicted in FIG. 1 when a double prodrug was incubated in rat plasma the ester functionality was cleaved by esterases almost immediately to liberate the carboxylic acid, while the ethoxycarbonyl moiety was very slow to convert to the free amidine.
Figure 2:
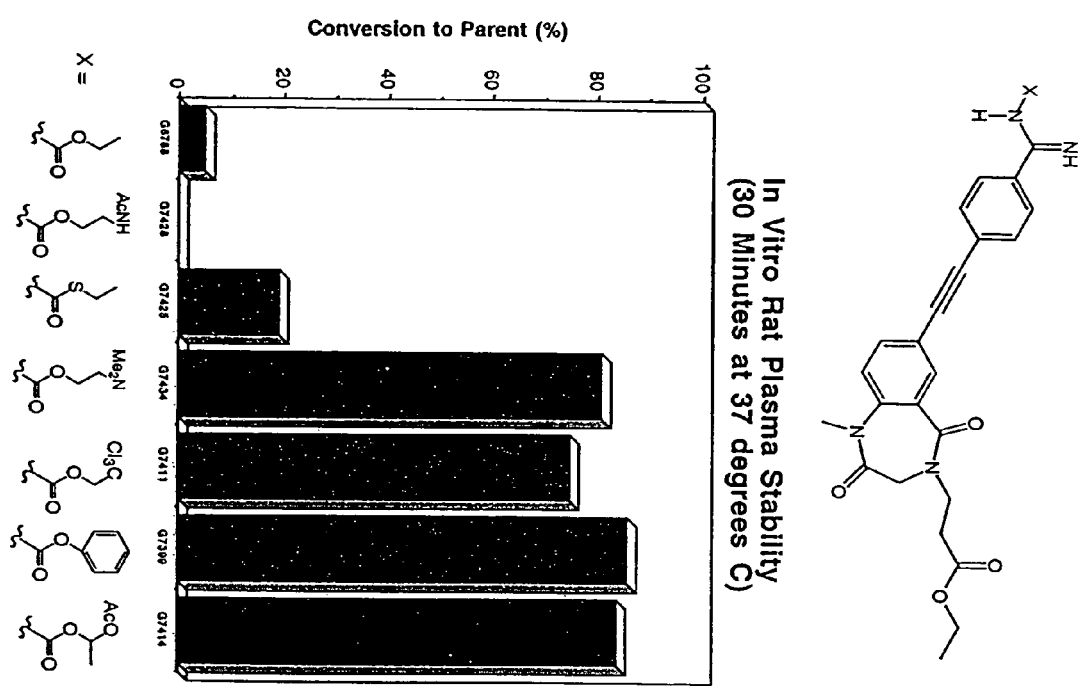
FIG. 2 is a graphic representation of the percent conversion of various prodrugs to bioactive parent compound in rat plasma after 30 minute incubation. The ability to cleave under physiological conditions was demonstrated for various alkoxycarbonyl derivatives of GPIIb/IIIa antagonists. Unlike simple alkoxycarbonylamidines such as the ethoxycarbonyl derivative (entry 1) the 2,2,2-trichloroethoxycarbonyl modified amidines (entry 5) cleave readily in rat plasma to yield the active metabolite.

The results for the G6249 based double prodrugs are shown in FIG. 2.

Conclusions

The electronically activated alkoxycarbonyl amidines (e.g trichloroethoxy, phenoxy) and the acyloxyalkoxy derivatives showed very good conversion (>10×) in comparison to the ethoxycarbonyl derivative. In the case of the acetoxyethoxy derivative almost complete conversion to the parent was observed within 30 minutes. Although the thioethoxycarbonyl derivative was superior to the simple ethoxycarbonyl derivative, this prodrug was poorer than most of the other derivatives. Similar plasma stability experiments with human plasma were consistent with the above results but absolute values were smaller, due in part to the lower levels of hydrolytic enzymes present in human plasma. Unlike simple alkoxycarbonylamidines such as ethoxycarbonyl derivative (FIG. 2, entry 1), the 2,2,2-trichloroethoxycarbonyl modified amidines (FIG. 2, entry 5) cleave readily in rat plasma to yield the active metabolite (FIG. 2). Similar enhancement in extent of cleavage was noted in human plasma with the 2,2,2-trichloroethoxy derivative cleaving to the active metabolite (3%) in 30 minutes where no active metabolite was observed with incubation of the ethoxycarbonyl derivative.

Figure 4:
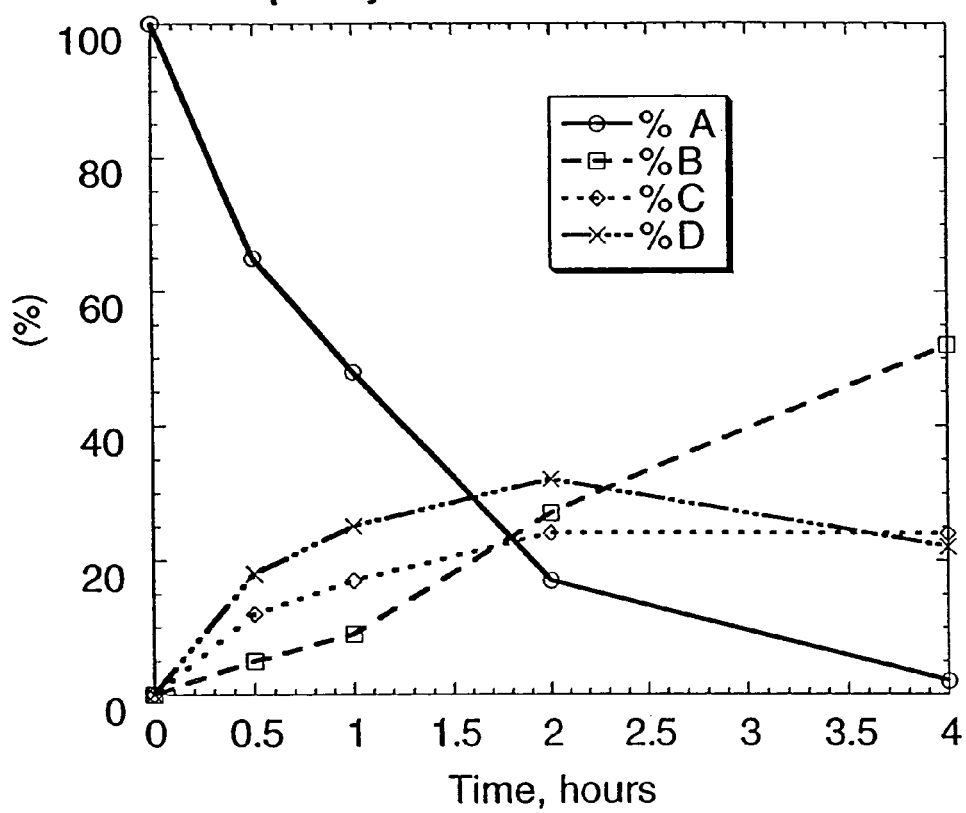
FIG. 4 depicts graphically the conversion of various prodrugs to the active parent in dog hepatocytes at 37 C. The 2,2,2-trichloroethoxycarbonylamidines effectively cleaves in dog hepatocytes to yield the bioactive parent compound.
Figure 4:
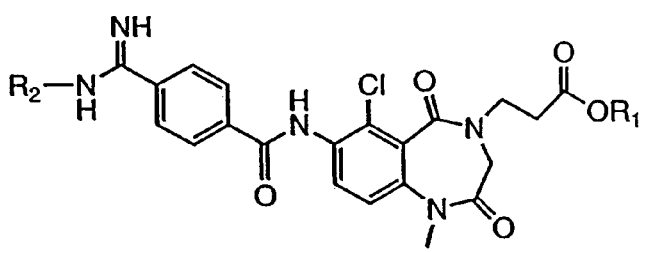

Similar in vitro results show that the 2,2,2-trichloroethoxycarbonylamidine effectively cleaves in dog hepatocytes to yield the active metabolite (FIG. 4).

Example 11

In Vivo Stability

Introduction

Studies were undertaken to assess the lability of the prodrugs in vivo.

Methods

To assess the lability of these modified alkoxycarbonyl prodrugs, several of the double prodrugs were injected at 2 mg/kg i.v. into rats and the percent conversion to the parent compound in the isolated plasma calculated after 6 hours.

Results

Figure 3:
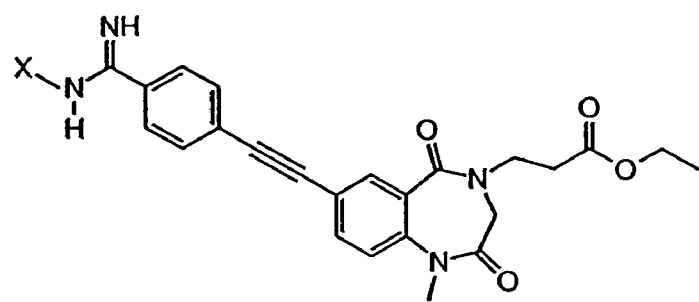
FIG. 3 graphically depicts the bioavailability (% F) upon intravenous administration of various prodrugs in rats at 2 mg/kg. Upon delivery of alkoxycarbonylamidine prodrugs by intravenous administration, simple alkylcarbamoyl amidines do not readily convert to the active metabolite whereas the 2,2,2-trichloroethoxycarbonyl derivatives cleaves to greater than 38%.
Figure 3:
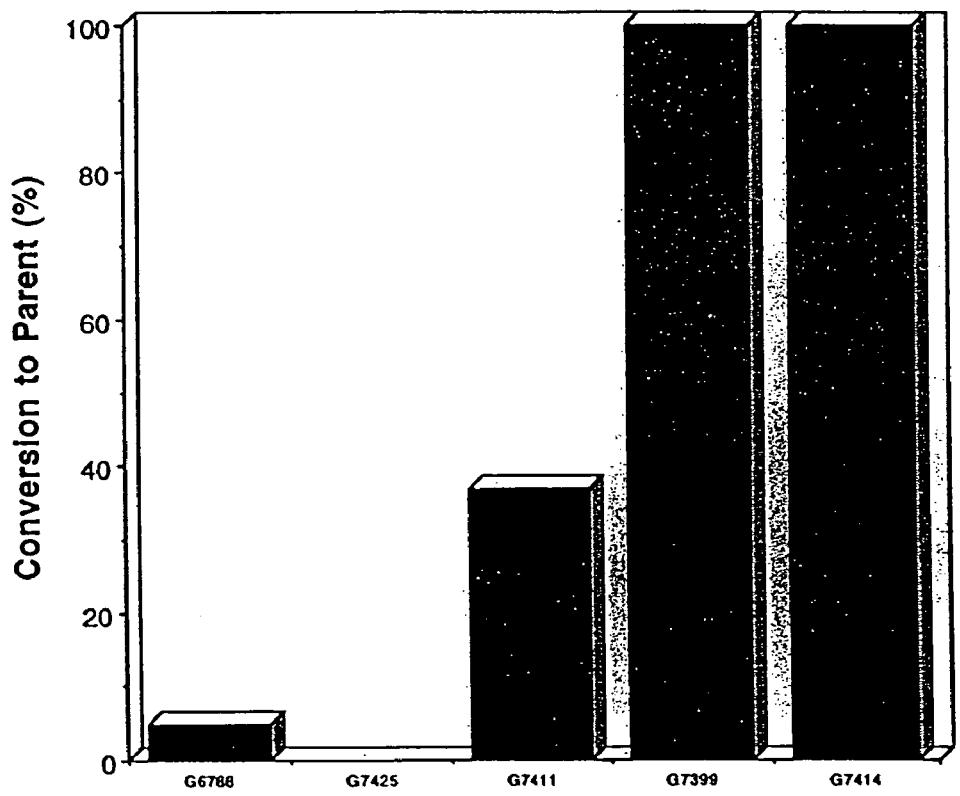
Figure 3:
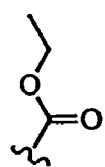
Figure 3:
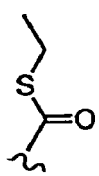
Figure 3:
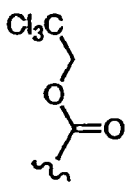
Figure 3:
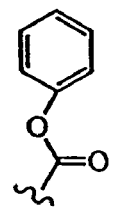
Figure 3:
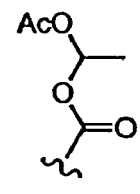

The results are presented in FIG. 3.

Conclusion

Consistent with the in vitro results, the acyloxyethoxy derivative showed quantitative conversion to the parent within 6 hours. Similarly the phenoxycarbonyl derivative was quantitatively converted to the parent. The trichloro ethoxy derivative was greater-than 8 times more labile than the ethoxy derivatve.

Example 12

Oral Bioavailability

Introduction

The double prodrugs where the amidine functionality is masked as a physiologically labile alkoxycarbonyl amidine were screened in a mouse assay to determine their oral bioavailability.

Methods

Oral bioavailability was assessed by dosing mice at 100 mg/kg orally and sacrificing the mice at either 1 or 3 hour timepoints. The mice were exsanguinated and ex vivo platelet aggregation measured by $ID_{50}$.

Results

FIG. 7 summarizes the $ID_{50}$ results.

Conclusion

From the data shown in FIG. 7 it can be seen that the acetoxyethoxycarbonyl derivative had a better $ID_{50}$ than the other derivatives in the G6249 series. The trichloroethoxycarbonyl and the trimethyl acetoxyethoxycarbonyl prodrugs had a positive effect on the G7464 series.

Example 13

Oral Bioavailability

Methods

Oral bioavailability was assessed by dosing dogs or rats at various concentrations orally and assessing the oral bioavailability at either 1 or 3 hour timepoints.

Results

Figure 5:
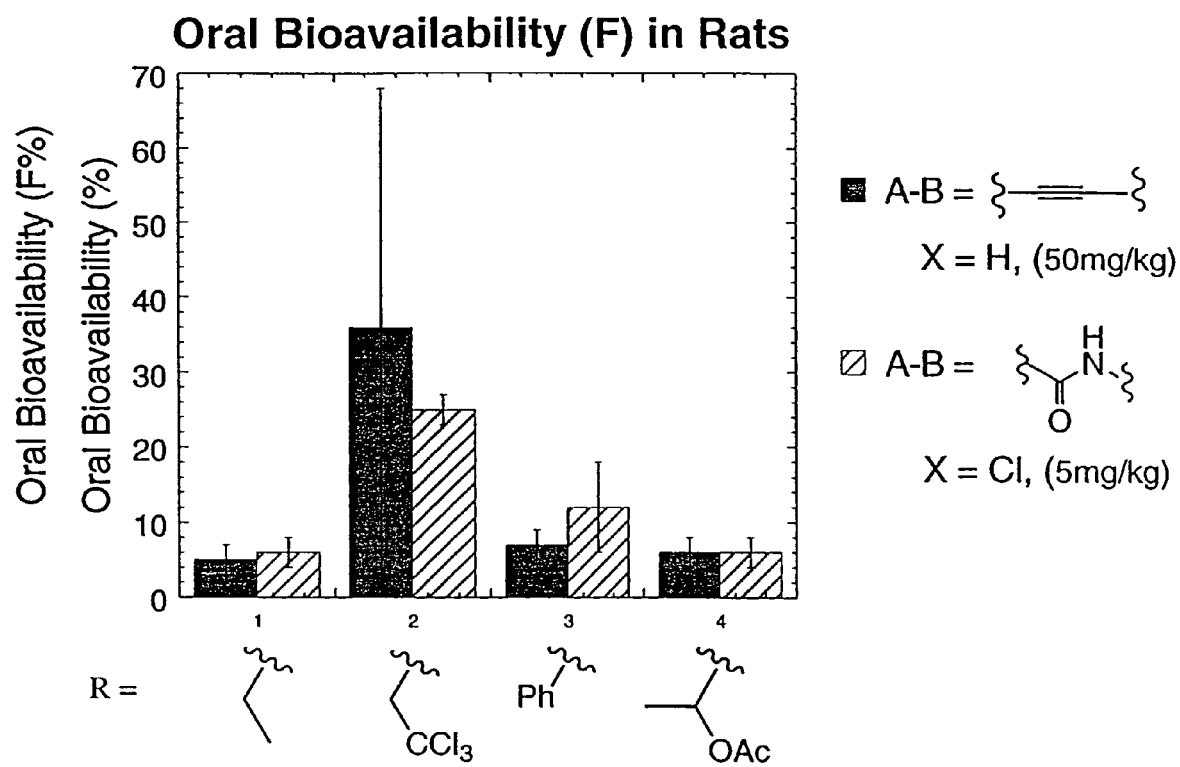
FIG. 5 graphically depicts bioavailability (% F) of compounds of the general formula I.

The results are presented in FIG. 5 and FIG. 6.

CONCLUSION

Of the various prodrugs prepared, the trichloroethoxy derivatives had the most profound effect on improving the oral bioavailability in the rats. While the acyloxyalkoxycarbonyl and the phenoxy carbonyl compounds had shown good conversion to the corresponding parent in plasma and i.v. prodrug experiments, they did not show good oral bioavailability in rats. It could be that these prodrugs are too labile and are prematurely hydrolyzed in the stomach or intestines prior to transport. It was only the trichloroethoxycarbonyl prodrugs that showed enhanced oral bioavailability in the rat. The trichloroethoxycarbonyl prodrugs provided a dramatic increase in oral bioavailability relative to their ethoxycarbonyl analogs.

FIG. 6 graphically depicts bioavailability of various prodrugs in dogs after oral administration. Use of the 2,2,2-trichloroethoxycarbonyl prodrug moiety doubled the oral bioavailability of compounds of the general structure (I) relative to the ethoxycarbonyl derivative when administereed orally at comparable doses to dogs. At lower doses the oral bioavailability increased to 29%.

What is claimed is:

1. A compound having the formula;

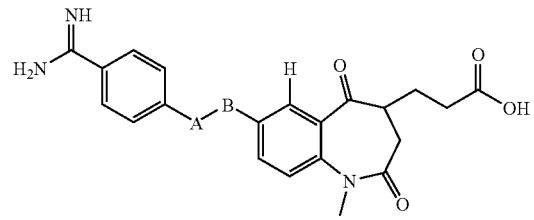

wherein -A-B- is selected from the group consisting of:

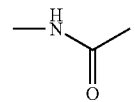

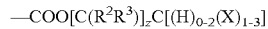

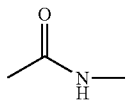

and the amidine group (—C(═NH)—NH$_2$) thereof is substituted with a prodrug moiety of the formula:

—COO[C(R$^2$R$^3$)]$_z$C[(H)$_{0-2}$(X)$_{1-3}$]

wherein [(H)$_{0-2}$(X)$_{1-3}$] is selected from the group consisting of X$_3$, HX$_2$, and H$_2$X and X is a halogen selected from the group consisting of F, Cl, Br, I or a combination thereof; and R$^2$ and R$^3$ are the same or different and are selected from the group consisting of H, C$_1$–C$_4$alkyl, C$_1$–C$_4$alkoxy, cyano, halo-C$_1$–C$_4$alkyl and aryl; and z is an integer from 1–5.

2. The compound of claim 1, wherein R$_2$ and R$_3$ are H.

3. The compound of claim 2, wherein [(H)$_{0-2}$(X)$_{1-3}$] is X$_3$ is Cl.

4. A compound selected from the group consisting of:
4H-1,4-Benzodiazepine-4-propanoic acid, 7-[[4-(N-2,2, 2-trichloroethoxycarbonylaminoiminomethyl)phenyl] methoxy]-1,2,3,5-tetrahydro-1 1-methyl-2,5-dioxo-, ethyl ester;

4H-1,4-Benzodiazepine-4-propanoic acid, 6-chloro-7-[[4-(N-2,2,2-trichloroethoxycarbonylaminoiminomethyl)benzoyl]amino]-1,2,3,5-tetrahydro-.beta.,1-dimethyl-2,5-dioxo-, ethyl ester;

4H-1,4-Benzodiazepine-4-propanoic acid, 7-[[4-(N-2,2,2-trichloroethoxycarbonylaminoiminomethyl)phenyl]ethynyl]-1-methyl-1,2,3,5-tetrahydro-2,5-dioxo-, ethyl ester; 4H-1,4-Benzodiazepine-4-propanoic acid, 6-chloro-7-[[(4-(N-2,2,2-trichloroethoxycarbonylaminoimnomethyl)benzoyl]amino])-1,2,3,5-tetrahydro-1-methyl-2,5-dioxo-, sec-butyl ester; and 4H-1,4-Benzodiazepine-4-propanoic acid, 6-chloro-7 [[4-(N-2,2,2-trichloroethoxycarbonylaminoimnomethyl)benzoyl]amino]-1,2,3,5-tetrahydro-.alpha.,1-dimethyl-2,5-dioxo-, ethyl ester.

5. A compound of formula I:

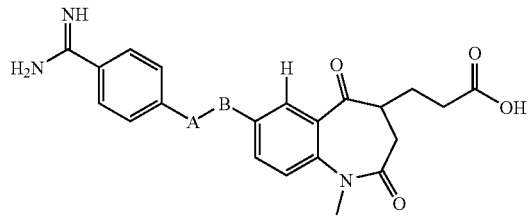

wherein -A-B- is selected from the group consisting of:

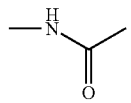

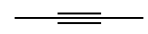

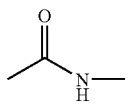 and $X'$ is H or Cl, and R is $-[C(R^2R^3)]_zC[(H)_{0-2}(X)_{1-3}]$ wherein $[(H)_{0-2}(X)_{1-3}]$ is selected from the group consisting of $X_3$, $HX_3$, and $H_2X$ and X is a halogen selected from the group consisting of F, Cl, Br, I or a combination thereof; and $R^2$ and $R^3$ are the same or different and are selected from the group consisting of H, $C_1$–$C_4$alklyl, $C_1$–$C_4$alkoxy, cyano, halo-$C_1$–$C_4$alkyl and aryl; and z is an integer from 1–5.

* * * * *